United States Patent
Kawaguchi et al.

(10) Patent No.: US 11,786,847 B2
(45) Date of Patent: Oct. 17, 2023

(54) FILTRATION DEVICE AND FILTRATION METHOD

(71) Applicant: Murata Manufacturing Co., Ltd., Nagaokakyo (JP)

(72) Inventors: Toshikazu Kawaguchi, Nagaokakyo (JP); Masaru Banju, Nagaokakyo (JP); Takashi Kondo, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 654 days.

(21) Appl. No.: 16/773,219

(22) Filed: Jan. 27, 2020

(65) Prior Publication Data

US 2020/0155981 A1    May 21, 2020

Related U.S. Application Data

(63) Continuation of application No. PCT/JP2018/032626, filed on Sep. 3, 2018.

(30) Foreign Application Priority Data

Sep. 19, 2017  (JP) .................................. 2017-179145
Sep. 25, 2017  (JP) .................................. 2017-183884

(51) Int. Cl.
*B01D 29/01* (2006.01)
*B01D 35/02* (2006.01)
(Continued)

(52) U.S. Cl.
CPC ............. *B01D 29/90* (2013.01); *B01D 29/01* (2013.01); *B01D 35/02* (2013.01); *B01L 3/0217* (2013.01);
(Continued)

(58) Field of Classification Search
CPC ............... A61M 1/3635; B01D 45/005; B01D 2201/32
See application file for complete search history.

(56) References Cited

U.S. PATENT DOCUMENTS

| 4,009,715 A | 3/1977 | Forberg et al. |
| 4,274,285 A | 6/1981 | Purgold |

(Continued)

FOREIGN PATENT DOCUMENTS

| CN | 201669063 U | 12/2010 |
| JP | H0657254 B2 | 8/1994 |

(Continued)

OTHER PUBLICATIONS

International Search Report issued for PCT/JP2018/032626, dated Nov. 27, 2018.

(Continued)

*Primary Examiner* — Bradley R Spies
(74) *Attorney, Agent, or Firm* — ArentFox Schiff LLP

(57) ABSTRACT

A filtration device includes a container, a channel member, and a filter. The container has a space of variable volume that contains a liquid, the liquid including a target substance to be separated by filtration. The channel member includes a channel and an opening that are defined therein, the opening being provided at a position along the channel in a direction transverse to the direction in which the channel extends. The channel member has an attachment part to which the container is attached and which provides communication between the space in the container and the channel. The filter is attached inside the channel member and positioned at the opening.

14 Claims, 27 Drawing Sheets

(51) Int. Cl.
  *B01L 3/00* (2006.01)
  *B01L 3/02* (2006.01)
  *B01D 29/90* (2006.01)
(52) U.S. Cl.
  CPC ....... *B01L 3/502* (2013.01); *B01L 2300/0681* (2013.01); *B01L 2300/0832* (2013.01)

(56) References Cited

U.S. PATENT DOCUMENTS

| | | |
|---|---|---|
| 5,914,042 A | 6/1999 | Ball et al. |
| 5,925,333 A | 7/1999 | Hooven et al. |
| 6,159,232 A | 12/2000 | Nowakowski |
| 6,274,090 B1 | 8/2001 | Coelho et al. |
| 7,056,722 B1 | 6/2006 | Coelho et al. |
| 7,650,805 B2 | 1/2010 | Nauseda et al. |
| 10,584,078 B2 | 3/2020 | Franci |
| 2006/0079834 A1 | 4/2006 | Tennican et al. |
| 2007/0079649 A1 | 4/2007 | Nauseda et al. |
| 2013/0225903 A1 | 8/2013 | Franci et al. |
| 2013/0264295 A1 | 10/2013 | Lee |
| 2015/0083665 A1 | 3/2015 | Oranth |
| 2016/0144105 A1 | 5/2016 | Hooven et al. |
| 2016/0257622 A1 | 9/2016 | Franci |
| 2018/0161497 A1 | 6/2018 | Hooven et al. |

FOREIGN PATENT DOCUMENTS

| | | |
|---|---|---|
| JP | 2003517272 A | 5/2003 |
| JP | 2006115//5 A | 5/2006 |
| JP | 2007105725 A | 4/2007 |
| JP | 2008515594 A | 5/2008 |
| JP | 2009106881 A | 5/2009 |
| JP | 2013217918 A | 10/2013 |
| JP | 2015516289 A | 6/2015 |
| JP | 2016524513 A | 8/2016 |
| JP | 6137438 B1 | 5/2017 |
| WO | 8909646 A1 | 10/1989 |
| WO | 2006130815 A2 | 12/2006 |
| WO | 2013098487 A1 | 7/2013 |
| WO | 2015071288 A1 | 5/2015 |
| WO | 2017104261 A1 | 6/2017 |

OTHER PUBLICATIONS

Written Opinion of the International Searching Authority issued for PCT/JP2018/032626, dated Nov. 27, 2018.
International Search Report issued for PCT/JP2018/031304, dated Nov. 27, 2018.
Written Opinion of the International Searching Authority issued for PCT/JP2018/031304, dated Nov. 27, 2018.

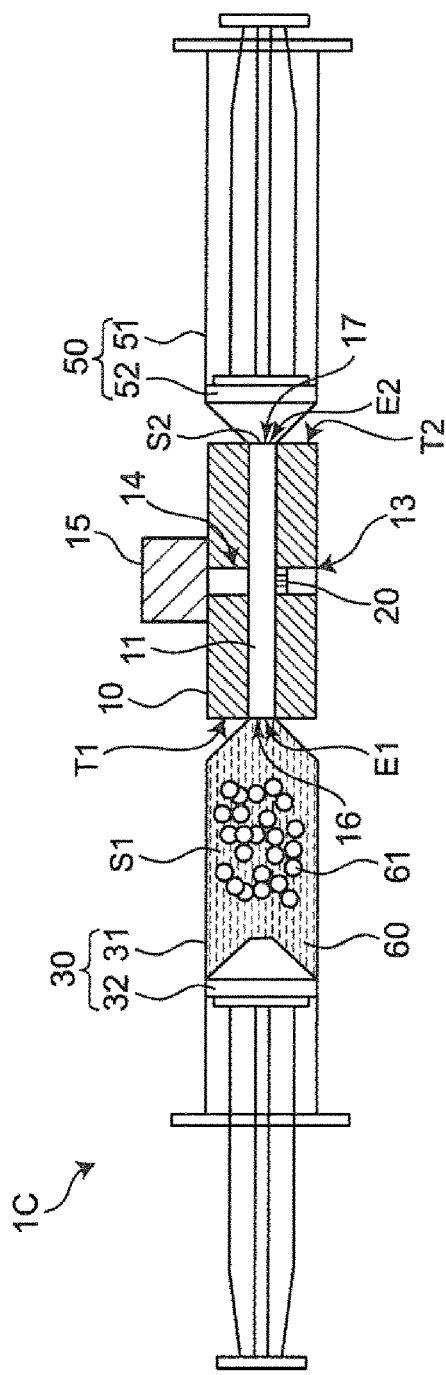

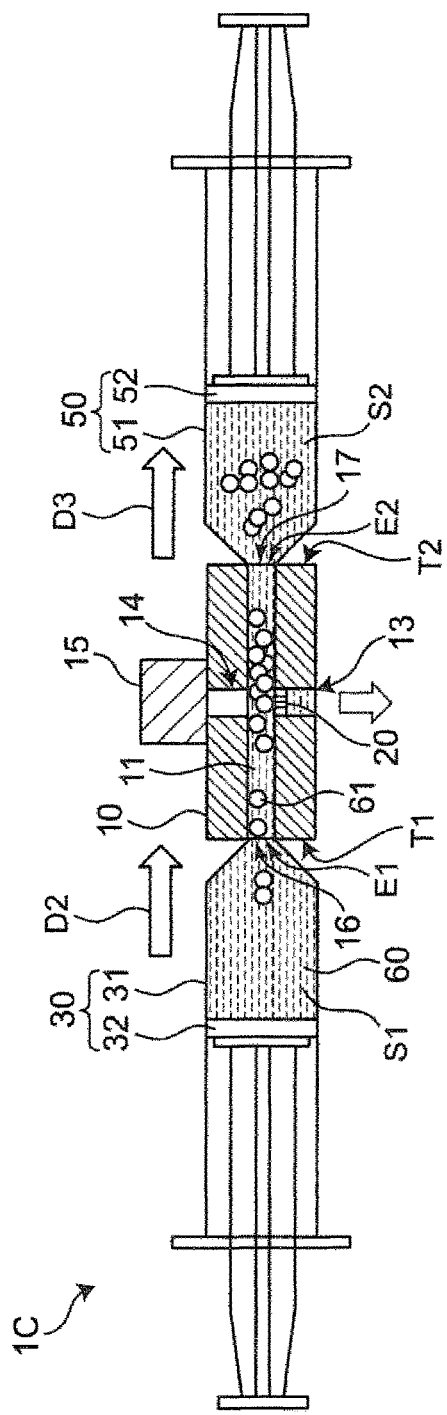

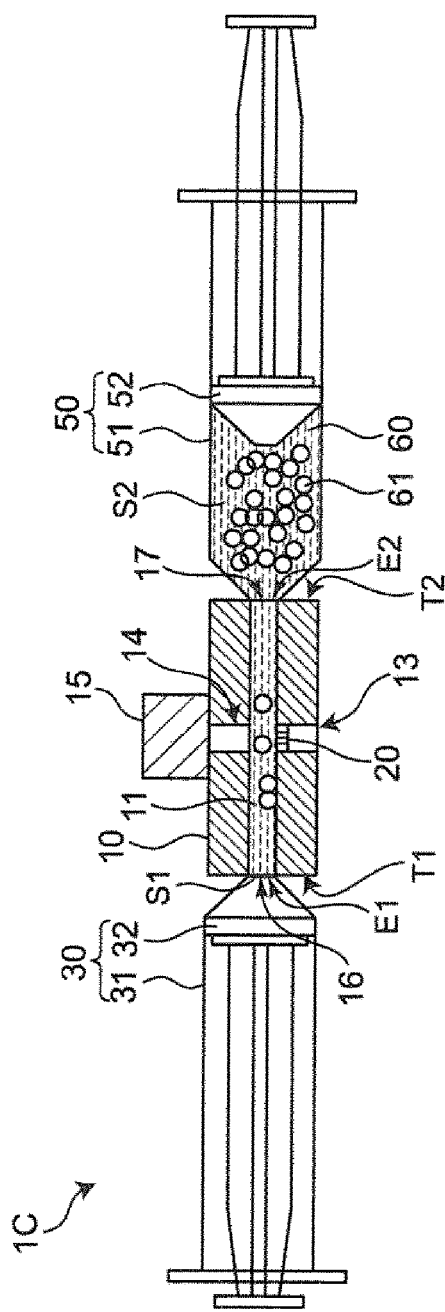

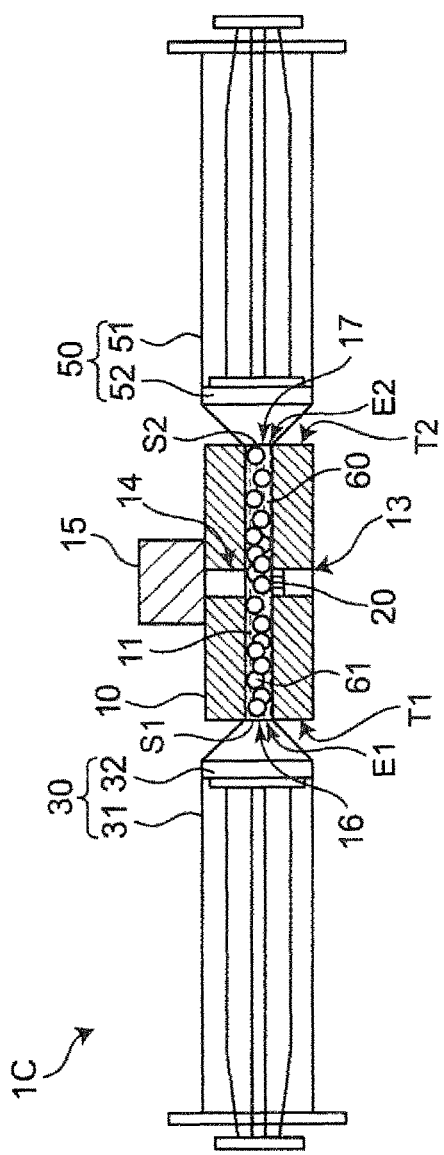

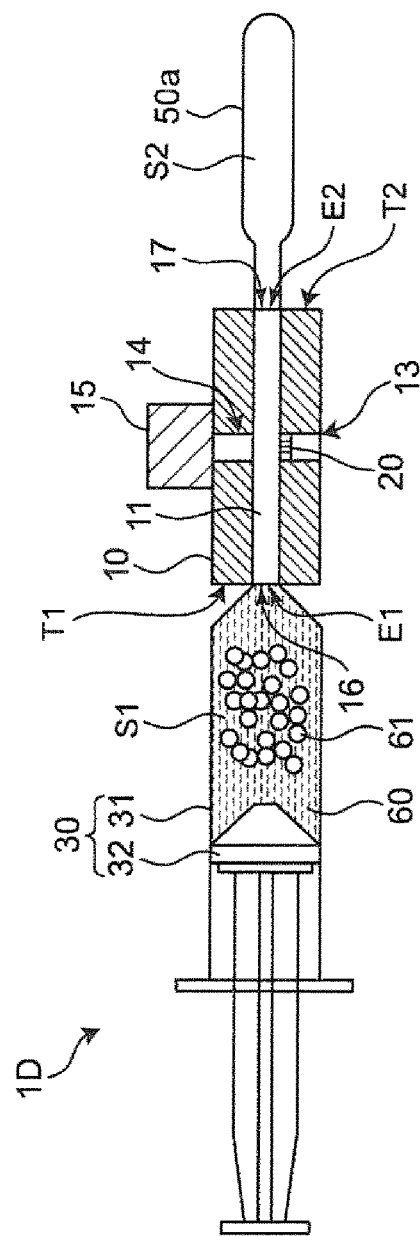

FILTRATION DEVICE AND FILTRATION METHOD

CROSS REFERENCE TO RELATED APPLICATIONS

The present application is a continuation of International application No. PCT/JP2018/032626, filed Sep. 3, 2018, which claims priority to Japanese Patent Application No. 2017-183884, filed Sep. 25, 2017, and Japanese Patent Application No. 2017-179145, filed Sep. 19, 2017, the entire contents of each of which are incorporated herein by reference.

FIELD OF THE INVENTION

The present invention relates to a filtration device, and a filtration method.

BACKGROUND OF THE INVENTION

Japanese Examined Patent Application Publication No. 6-57254 (Patent Document 1) discloses a filtration device with a circulating system. The circulating system includes a container containing a liquid including blood components, and a ceramic filter. The filtration device is used for cross-flow filtration of the liquid including blood components. In the filtration device according to this published application, a pump is disposed between the container and the filter, and these components are connected by a tube or other piping to form the circulating system. Unfortunately, the foregoing filtration device still leaves room for improvement in that the filtration device does not readily allow filtration of a desired volume of liquid.

BRIEF SUMMARY OF THE INVENTION

It is an object of the present invention to provide a filtration device and a filtration method that enable filtration of a desired volume of liquid.

In the filtration device according to Patent Document 1, the container containing the liquid to be filtered, the filter, and the pump are connected by a tube or other piping to form the circulating system. The pump is used to supply the liquid from the container to the filter via the piping to thereby filter the liquid.

In this filtration device the volume of liquid to be filtered depends on the volume of the piping. It is difficult for this filtration device to filter a liquid volume that is less than the volume of the piping. Thus, it is difficult for this filtration device to filter a very small volume of liquid, for example, 1 ml or less.

The present inventors have found that a desired volume of liquid can be filtered by supplying, without use of piping, a liquid including a target substance from a container with a variable-volume space containing the liquid, to a channel in a channel member to which a filter is attached.

A filtration device according to an aspect of the present invention includes:
a container having a space of variable volume that can contain a liquid which includes a target substance to be separated by filtration;
a channel member having a channel and an opening extending from the channel to a position outside of the channel member, the channel member having an attachment part to which the container is attached and which provides fluid communication between the space in the container and the channel; and
a filter attached inside the channel member and positioned at the opening.

A filtration method according to an aspect of the present invention includes the steps of:
supplying liquid contained in the container to the channel by changing a volume of the space in the container; and
passing at least part of the liquid through the filter.

The supplying step includes passing the liquid through the filter.

The present invention makes it possible to provide a filtration device and a filtration method that enable filtration of a desired volume of liquid.

A filtration device according to an aspect of the present invention includes:
a container having a space of variable volume to contain a liquid, the liquid including a target substance to be separated by filtration;
a channel member including a channel and an opening that are defined inside the channel member, the opening being provided at a position along the channel in a direction transverse to a direction in which the channel extends, the channel member having an attachment part to which the container is attached and which provides communication between the space in the container and the channel; and
a filter attached inside the channel member and positioned at the opening.

The above-mentioned configuration enables filtration of a desired volume of liquid.

In one possible configuration of the filtration device,
at least a portion of an inner wall of the container is movable, and
by moving the inner wall of the container, a volume of the space is changed to allow supply of the liquid to the channel.

The above-mentioned configuration facilitates supply of the liquid in the container to the channel.

In one possible configuration of the filtration device,
the channel member has one end and another end,
the one end of the channel member is provided with the attachment part, and
the other end of the channel member is provided with a closing member that closes the channel.

The above-mentioned configuration facilitates passage of the liquid through the filter.

The container may be a syringe.

The above-mentioned configuration makes it easier to change the volume of the space.

In one possible configuration of the filtration device,
the container is a first container,
the space of the first container is a first space,
the attachment part is a first attachment part,
the filtration device further includes a second container having a second space of variable volume,
the channel member has a second attachment part to which the second container is attached and which provides communication between the second space in the second container and the channel,
the channel member has one end and another end,
the one end of the channel member is provided with the first attachment part,
the other end of the channel member is provided with the second attachment part, and
the second space of the second container contains the liquid including the target substance that has moved to the second container from the first container via the channel.

The above-mentioned configuration allows the liquid including the target substance to reciprocate between the first and second containers via the channel of the channel member. This enables filtration of a desired volume of liquid while reducing pressure on the target substance.

In one possible configuration of the filtration device, at least a portion of an inner wall of the second container is movable, and by moving the inner wall of the second container, a volume of the second space in the second container is changed to allow supply of the liquid to the channel.

The above-mentioned configuration facilitates supply of the liquid contained in the second space in the second container to the channel.

In one possible configuration of the filtration device, at least one of the first container and the second container is a syringe.

The above-mentioned configuration makes it easier to change the volume of at least one of the space in the first container and the space in the second container.

In one possible configuration of the filtration device, the channel member includes a first channel member having a recess recessed inward from an outer wall surface, a groove having an opening in a recessed surface of the recess, a first channel and a second channel, the first and second channels each being defined by a through-hole connected to the groove, a first connection part that connects the groove with the first channel, and a second connection part that connects the groove with the second channel, and a second channel member having a projection that detachably mates with the recess of the first channel member, the second channel member including a discharge channel, the discharge channel having an opening in a projecting surface of the projection placed over the groove of the first channel member, a third channel is formed by positioning the projecting surface of the projection of the second channel member over the opening of the groove of the first channel member, the third channel is connected to the first channel via the first connection part, and connected to the second channel via the second connection part, the third channel has a smaller cross-sectional area than the first channel and the second channel, the filter is positioned at the third channel, the first space in the first container communicates with the first channel, and the second space in the second container communicates with the second channel.

The above-mentioned configuration makes it possible to minimize an increase in the velocity of the liquid through the first and second channels while increasing the velocity of the liquid through the third channel that faces the filter. This helps reduce clogging of the filter by the target substance.

A filtration method according to an aspect of the present invention includes the steps of:

providing a filtration device, the filtration device including a container having a space of variable volume to contain a liquid, the liquid including a target substance to be separated by filtration, a channel member including a channel and an opening that are defined inside the channel member, the opening being provided at a position along the channel in a direction transverse to a direction in which the channel extends, the channel member having an attachment part to which the container is attached and which provides communication between the space in the container and the channel, and a filter attached inside the channel member and positioned at the opening; and supplying the liquid contained in the container to the channel by changing a volume of the space in the container.

The supplying step includes passing the liquid through the filter.

The above-mentioned configuration enables filtration of a desired volume of liquid.

In one possible configuration of the filtration method, the providing step includes providing the filtration device in which the container is a first container, the space of the first container is a first space, and the attachment part is a first attachment part, and which further includes a second container having a second space of variable volume, the channel member having a second attachment part to which the second container is attached and which provides communication between the second space in the second container and the channel, the channel member having one end and another end, the one end of the channel member being provided with the first attachment part, the other end of the channel member being provided with the second attachment part, and the supplying step includes moving the liquid contained in the first space in the first container to the second space in the second container via the channel.

The above-mentioned configuration enables filtration of a desired volume of liquid while reducing pressure on the target substance.

In one possible configuration of the filtration method, the filtration method further includes the step of supplying the liquid contained in the second space in the second container to the channel by changing a volume of the second space in the second container, and the step of supplying the liquid contained in the second space in the second container to the channel includes moving the liquid contained in the second space in the second container to the first space in the first container via the channel, and passing the liquid through the filter.

The above-mentioned configuration allows the liquid including the target substance to reciprocate between the first and second containers via the channel of the channel member. This enables filtration of a desired volume of liquid while reducing pressure on the target substance.

In one possible configuration of the filtration method, the filtration method further includes the step of repeating the step of supplying the liquid contained in the first space in the first container to the channel, and repeating the step of supplying the liquid contained in the second space in the second container to the channel.

The above-mentioned configuration allows the liquid including the target substance to reciprocate a plurality of times between the first and second containers via the channel of the channel member. This enables more efficient filtration of a desired volume of liquid while further reducing pressure on the target substance.

In one possible configuration of the filtration method, the filtration method further includes the step of collecting the target substance present in the channel.

The above-mentioned configuration makes it possible to filter a desired volume of the liquid to collect the target substance.

BRIEF DESCRIPTION OF DRAWINGS

FIG. 10A illustrates an exemplary step in the filtration method according to Embodiment 2 of the present invention.

FIG. 10B illustrates an exemplary step in the filtration method according to Embodiment 2 of the present invention.

FIG. 10C illustrates an exemplary step in the filtration method according to Embodiment 2 of the present invention.

FIG. 10E illustrates an exemplary step in the filtration method according to Embodiment 2 of the present invention.

FIG. 11 is a schematic diagram of a filtration device according to a modification of Embodiment 2 of the present invention.

DETAILED DESCRIPTION OF THE PREFERRED EMBODIMENTS

Embodiment 1

Figure 1:
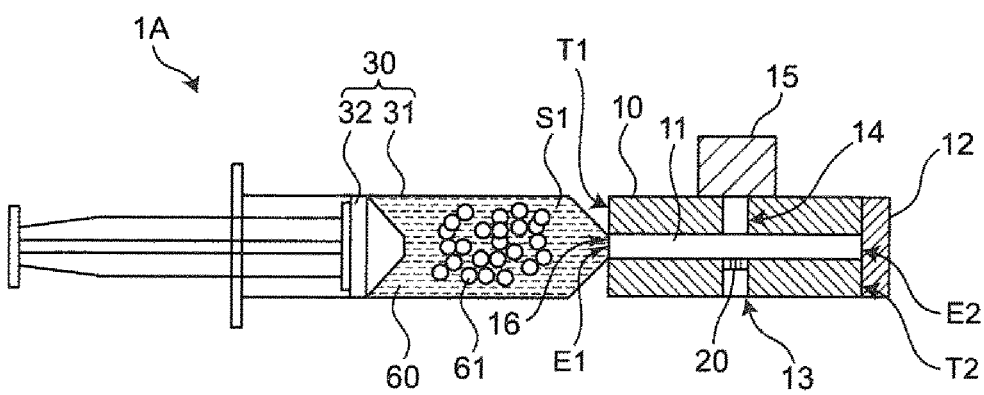
FIG. 1 is a schematic diagram of a filtration device according to Embodiment 1 of the present invention.

Referring now to the drawings wherein like numerals indicate like elements, embodiment 1 of the present invention will be described below with reference to FIGS. 1-7. In the drawings, the elements are shown in exaggerated form for ease of description.

FIG. 1 is a schematic diagram of a filtration device 1A according to Embodiment 1 of the present invention. As illustrated in FIG. 1, the filtration device 1A filters a liquid 60 including a target substance 61. The filtration device 1A includes a channel member 10, a filter 20 attached inside the channel member 10, and a container 30 attached to the channel member 10. In Embodiment 1, the container 30 is directedly attached to the channel member 10 without using another intervening tube or other piping.

The term "target substance" as used herein refers to, among substances included in a liquid, a substance to be separated by filtration. For example, the target substance 61 may be a biologically derived substance included in a liquid. The term "biologically derived substance" as used herein refers to a substance derived from living organisms such as cells (eukaryotes), bacteria (eubacteria), or viruses. Examples of cells (eukaryotes) include induced pluripotent stem cells (iPS cells), ES cells, stem cells, mesenchymal stem cells, mononuclear cells, single cells, cell clusters, suspension cells, adherent cells, nerve cells, white blood cells, cells for regenerative medicine, autologous cells, cancer cells, circulating tumor cells in blood (CTC), HL-60, HELA, and fungi. Examples of bacteria (eubacteria) include *E. coli*, and *Mycobacterium tuberculosis*.

In the example of Embodiment 1, the liquid 60 is a cell culture solution, and the target substance 61 is a cell.

The channel member 10 includes a channel 11 and an opening 13, which are defined inside the channel member 10. The opening 13 is provided at a position along the channel 11 in a direction transverse to the direction in which the channel 11 extends. The channel member 10 has an attachment part 16 to which the container 30 is attached and which provides communication between a space S1 in the container 30 and the channel 11.

The channel member 10 has one end T1, and another end T2. The one end T1 of the channel member 10 is provided with the attachment part 16 to which the container 30 is attached, and the other end T2 is provided with a closing member 12. The channel member 10 can be made of, for example, polycarbonate, polyoxymethylene, or acrylic.

The channel 11 extends from the one end T1 of the channel member 10 toward the other end T2. The channel 11 has, for example, a circular cross-section. The channel 11 extends through the attachment part 16. The container 30 is attached to one end E1 of the channel 11 located at the one end T1 of the channel member 10. Another end E2 of the channel 11, which is located at the other end T2 of the channel member 10, is closed by the closing member 12. The channel 11 is connected to the opening 13 and to a collection hole 14 used to collect the target substance 61.

The channel 11 is designed to have a volume such that when filtration is finished, a desired volume of the liquid 60 including the target substance 61 remains in the channel 11. In Embodiment 1, the channel 11 of the channel member 10 has a volume of, for example, 0.4 ml.

The closing member 12 closes the other end E2 of the channel 11. The closing member 12 blocks the channel 11 to prevent the liquid 60 from leaking through the other end E2 of the channel 11. More specifically, the closing member 12 is provided at the other end T2 of the channel member 10.

The opening 13 is a hole provided at a position along the length of the channel 11 and extends in direction transverse to the direction in which the channel 11 extends. More specifically, the opening 13 extends from the middle portion of the channel 11 radially outward toward the bottom (as viewed in FIG. 1) of the outer surface of the channel member 10 so as to provide communication between the channel 11 and the outside of the channel member 10. In other words, the opening 13 serves as a discharge channel for discharging the liquid 60 with the target substance 61 remaining in the channel 11.

The collection hole 14 is used to collect the target substance 61 remaining in the channel 11 after filtration is finished. Like the opening 13, the collection hole 14 extends in a direction transverse to the direction in which the channel 11 extends. The collection hole 14 is closed with a cap 15. In Embodiment 1, the collection hole 14 is provided in a direction orthogonal to the direction in which the channel 11 extends. More specifically, the collection hole 14 extends from the middle portion of the channel 11 toward the top (as viewed in FIG. 1) of the outer surface of the channel member 10. The collection hole 14 provides communication between the channel 11 and the outside of the channel member 10.

The attachment part 16 is provided at the one end T1 of the channel member 10. The attachment part 16, which receives the container 30 attached thereto, provides communication between the space S1 in the container 30 and the channel 11. The attachment part 16 is shaped to allow attachment of the container 30 to the attachment part 16. More specifically, the attachment part 16 is shaped to conform to the shape of the distal end of the container 30. The one end E1 of the channel 11, which extends through the attachment part 16, is located inside the attachment part 16. As a result, when the container 30 is attached to the attachment part 16, the space S1 in the container 30 communicates with the channel member 10.

The filter 20 is used to separate the target substance 61 included in the liquid 60 from the liquid 60 and maintain it in the channel 11. To this end, the filter 20 is preferably attached inside the channel member 10, and positioned at proximal end of the opening 13. More specifically, the filter 20 is attached at the connection between the channel 11 of the channel member 10 and the opening 13. In Embodiment 1, the filter 20 is preferably a porous membrane made of metal.

Figure 2:
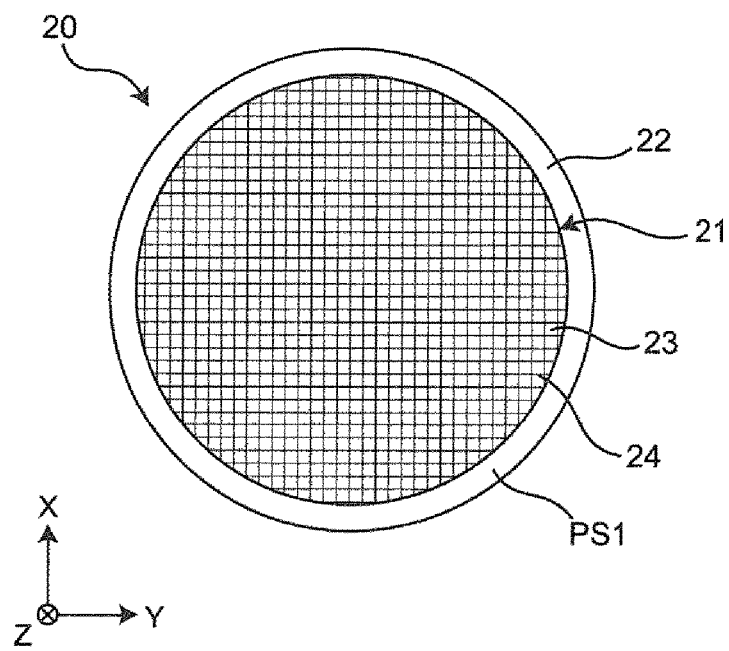
FIG. 2 is a schematic diagram of a filter.
Figure 3:
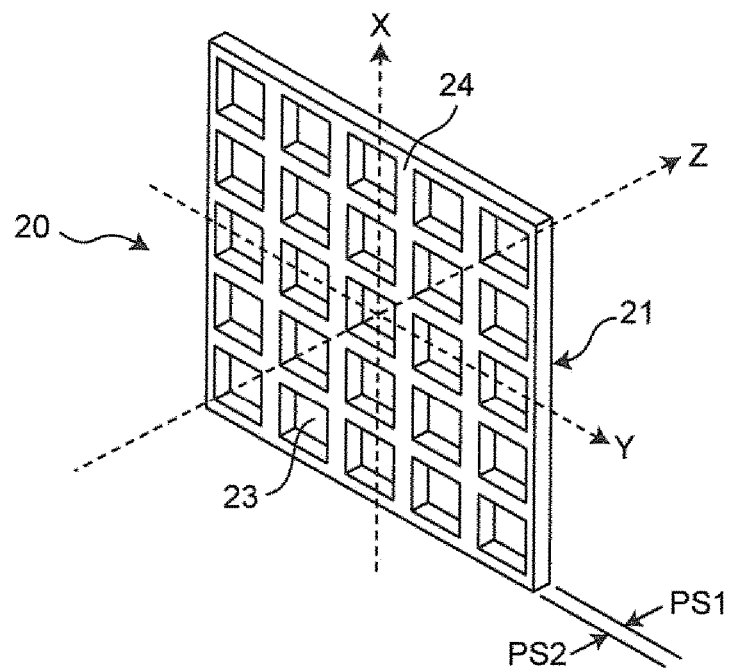
FIG. 3 is an enlarged perspective view of a portion of a filter.

FIG. 2 is a schematic plan view of the filter 20. FIG. 3 is an enlarged perspective view of a portion of the filter 20. The X, Y, and Z directions in FIGS. 2 and 3 respectively represent the lateral, longitudinal, and thickness directions of the filter 20.

As illustrated in FIG. 2, the filter 20 includes a filtering part 21 and a holding part (a frame) 22 disposed on the outer periphery of the filtering part 21. As illustrated in FIG. 3 (which is a square partial view of the filtering part), the filtering part 21 includes a filtering body party 24 having opposed first and second major surfaces PS1 and PS2. In the example of Embodiment 1, the first major surface PS1 is a flat surface which, when the filter 20 is placed in operational contact with the channel member 10 will be flush with the side wall of the channel 11.

The filtering body part 24, which forms the body portion of the filter 20, is preferably made of a material mainly containing a metal and/or a metal oxide. For example, the filtering body part 24 may be made of gold, silver, copper, platinum, nickel, palladium, titanium, or an alloy or oxide thereof.

The filter 20 may have, for example, a circular, rectangular, or elliptical outer shape. In Embodiment 1, the filter 20 has a substantially circular outer shape as illustrated in FIG. 2. The term "substantially circular" as used herein refers to a shape such that the ratio of the length along the major axis to the length along the minor axis ranges from 1.0 to 1.2.

The filtering part 21 is a plate-like structure provided with through-holes 23 which extend from the first to the second major surface PS1 and PS2 so that fluid can pass through the through holes. The filtering part 21 has, for example, a circular, rectangular, or elliptical shape. In Embodiment 1, the filtering part 21 has a substantially circular shape.

Figure 4:
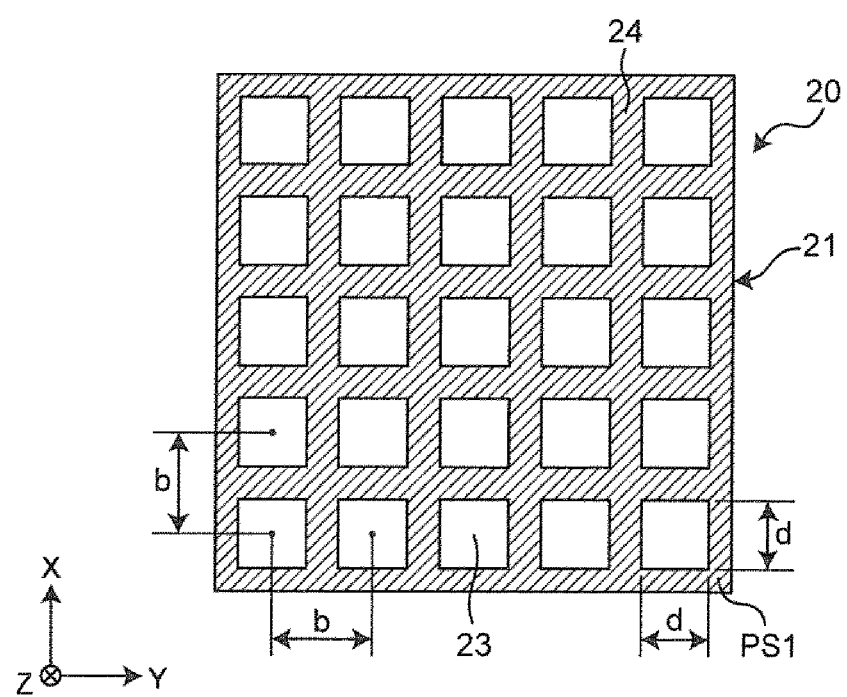
FIG. 4 is a schematic view of the portion of the filter illustrated in FIG. 3 as seen in the direction of its thickness.

FIG. 4 is a schematic view of the portion of the filter 20 illustrated in FIG. 3 as seen in the direction of its thickness (Z direction). As illustrated in FIG. 4, the through-holes 23 are preferably arranged periodically in the first and second major surfaces PS1 and PS2 of the filtering part 21. More specifically, the through-holes 23 are arranged in the filtering part 21 in a matrix at regular intervals.

In the example shown in Embodiment 1, the through-holes 23 have a square shape as viewed from the first major surface PS1 of the filtering part 21, that is, as viewed in the Z direction. The through-holes 23 can have other shapers such as a rectangular, circular, or elliptical shape.

In Embodiment 1, the through-holes 23 have a rectangular shape (in cross section) as projected onto a plane perpendicular to the first major surface PS1 of the filtering part 21. More specifically, the cross-section of the through-holes 23 is a rectangle whose one side in the radial direction of the filter 20 is longer than one side in the thickness direction of the filter 20. The through-holes 23 may have other shapes, for example, a tapered cross-section such as a parallelogram or a trapezoid, or may have a symmetrical or asymmetrical cross-section.

In Embodiment 1, the through-holes 23 are arrayed with equal pitches in two directions parallel to the sides of their square shape as viewed from the first major surface PS1 of the filtering part 21 (Z direction), that is, in the X and Y directions in FIG. 4. Arranging the through-holes 23 in a square lattice array as described above allows for increased open area percentage, and consequently reduced resistance of the filter 20 to the passage of liquid. This configuration helps shorten filtration time, thus reducing stress on the target substance 61.

The through-holes 23 do not have to be arranged in a square lattice array, and may be arranged in other types of arrays, for example, a quasi-periodic array or periodical array. Examples of periodic arrays may include any quadrangular arrays, such as rectangular arrays with different pitches in two array directions, and triangular or regular triangular lattice arrays. The through-holes 23 may be arrayed in any fashion as long as the filtering part 21 is provided with a plurality of through-holes 23.

The pitch of the through-holes 23 is designed as appropriate in accordance with the type (e.g., size, morphology, properties, or elasticity) and volume of the cells to be separated. The pitch of the through-holes 23 is herein defined as described below. As illustrated in FIG. 4, with the through-holes 23 viewed from the first major surface PS1 of the filtering part 21, the pitch of the through-holes 23 refers to the distance b between the center of a given through-hole 23 and the center of the adjacent through-hole 23. For periodically arrayed structures, the pitch b of the through-holes 23 is, for example, more than 1 time and not more than 10 times the size of one side "d" of each through-hole 23, preferably not more than 3 times the size of one side "d" of each through-hole 23. Alternatively, the filtering part 21 has an open area percentage of, for example, 10% or more, preferably 25% or more. This configuration can reduce the resistance of the filtering part 21 to the passage of liquid. This helps shorten filtration time, thus reducing stress on the cells. The open area percentage is calculated as the area occupied by the through-holes 23 divided by the projected area of the first major surface PS1 that is assumed to have no through-hole 23.

The filtering part 21 preferably has a thickness more than 0.1 times and not more than 100 times the size (of the one side "d") of each through-hole 23. More preferably, the filtering part 21 has a thickness more than 0.5 times and not more than 10 times the size (of the one side "d") of each through-hole 23. This configuration can reduce the resistance of the filter 20 to the passage of liquid, thus shortening filtration time. As a result, stress on the target substance 61 can be reduced.

In the filtering part 21, the first major surface PS1 in contact with the liquid including the target substance 61 preferably has a small surface roughness. The term surface roughness as used herein refers to the mean of the differences between the maximum and minimum values measured with a stylus profilometer at five given points on the first major surface PS1. In Embodiment 1, the surface roughness is preferably smaller than the size of the target substance 61, more preferably smaller than half the size of the target substance 61. In other words, the openings defined in the first major surface PS1 of the filtering part 21 by the through-holes 23 are formed in the same plane (XY-plane). The filtering body part 24, which is a portion of the filtering part 21 with no through-hole 23, is formed as a continuous, integral part. This configuration helps reduce deposition of the target substance 61 on the surface (first major surface PS1) of the filtering part 21, resulting in reduced resistance to the flow of the liquid 60.

In the filtering part 21, the opening of each through-hole 23 in the first major surface PS1 communicates with the opening of the through-hole 23 in the second major surface PS2 via a continuous wall surface. More specifically, each through-hole 23 is provided such that the opening of the through-hole 23 in the first major surface PS1 can be projected onto the opening of the through-hole 23 in the second major surface PS2. In other words, each through-hole 23 is provided such that, with the filtering part 21 viewed from the first major surface PS1, the opening of the through-hole 23 in the first major surface PS1 overlaps the opening of the through-hole 23 in the second major surface PS2. In Embodiment 1, each through-hole 23 is provided such that its inner wall is perpendicular to the first and second major surfaces PS1 and PS2.

The holding part 22 is preferably disposed on the outer periphery of the filtering part 21 and may be thicker than the filtering part 21. This configuration increases the mechanical strength of the filter 20.

The holding part 22 serves as a connection part that connects the filter 20 with a holder (not illustrated). In Embodiment 1, the holding part 22 of the filter 20 is held by the holder in attaching the filter 20 to the opening 13.

As seen in FIG. 2, the holding part 22 is ring-shaped as viewed from the first major surface PS1 of the filtering part 21. With the filter 20 viewed from the first major surface PS1, the center of the holding part 22 coincides with the center of the filtering part 21. In other words, the holding part 22 is formed concentrically with the filtering part 21.

Information on the filter (e.g., the dimensions of the through-holes 23) may be indicated on the holding part 22.

Returning to FIG. 1, the container 30 is used to hold the liquid 60 containing the target substance 61. The container 30 is attached to the attachment part 16 provided at the one end T1 of the channel member 10. The container 30 is thus attached to the one end E1 of the channel 11 of the channel member 10. The container 30 includes the space S1 of variable volume defined therein to contain the liquid 60 including the target substance 61. The attachment part 16 thus provides communication between the space S1 in the container 30 and the channel 11 of the channel member 10.

In the state before filtration, that is, in the state before a change in volume of the container 31, the space S1 in the container 30 has a larger volume than the channel 11 of the channel member 10. In the state after filtration has been completed, that is, in the state after a change in volume of the space S1 in the container 30, the space S1 in the container 30 has a smaller volume than the channel 11 of the channel member 10. The state before a change in volume refers to, for example, the state where the space S1 in the container 30 is at its maximum volume. The state after a change in volume refers to the state where the container 30 has undergone the maximum change and no further deformation is possible. In Embodiment 1, the volume of the space S1 in the container 30 is variable (as the plunger 32 is moved) from, for example, 0 to 5 ml.

The space S1 is closed except for the portion where the container 30 is attached to the channel member 10. More specifically, the space S1 is open only in its portion where the container 30 is attached to the one end T1 of the channel member 10. In other words, the space S1 is open only in its portion that communicates with the channel 11 of the channel member 10.

In Embodiment 1, the container 30 is formed as a syringe. More specifically, the container 30 includes an outer cylinder 31, and a plunger 32 that is movable within the outer cylinder 31. A gasket is attached at the distal end of the plunger 32. This configuration makes it easier to change the volume of the space S1.

In the container 30, the inside of the outer cylinder 31, and the plunger 32 define the space S1 of variable volume. For example, for the container 30, the space S1 in the outer cylinder 31 can be decreased in volume by pushing the plunger 32 disposed inside the outer cylinder 31. The liquid 60 contained in the space S1 in the container 30 can be thus supplied to the channel 11 of the channel member 10. For the container 30, the space S1 in the outer cylinder 31 can be increased in volume by pulling the plunger 32 disposed inside the outer cylinder 31. The liquid 60 can be thus contained in the space S1 in the container 30.

Figure 5:
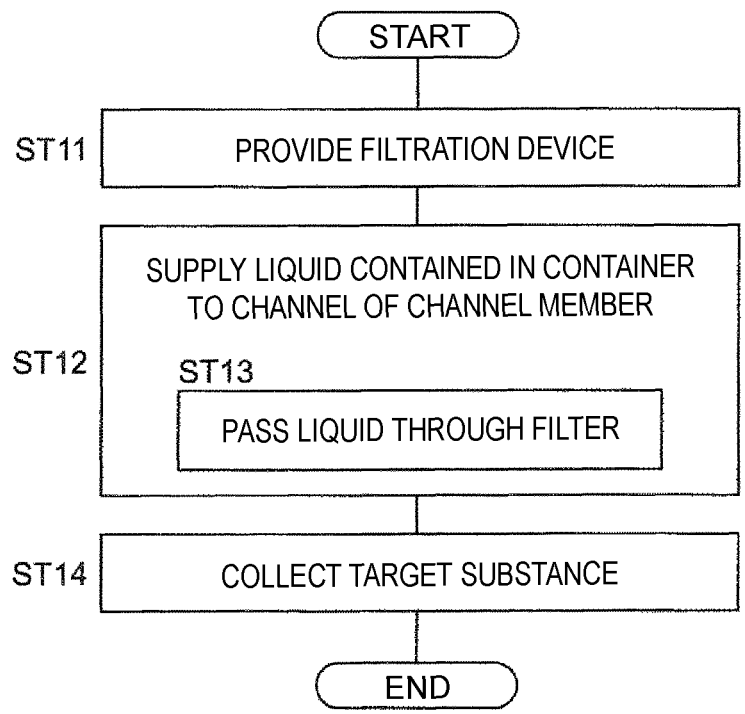
FIG. 5 is an exemplary flowchart of a filtration method according to Embodiment 1 of the present invention.

A filtration method using the filtration device 1A will be described below with reference to FIG. 5 and FIGS. 6A to 6E. FIG. 5 is an exemplary flowchart of a filtration method according to Embodiment 1 of the present invention. FIGS. 6A to 6E each illustrate an exemplary step in the filtration method according to Embodiment 1 of the present invention.

Figure 6A:
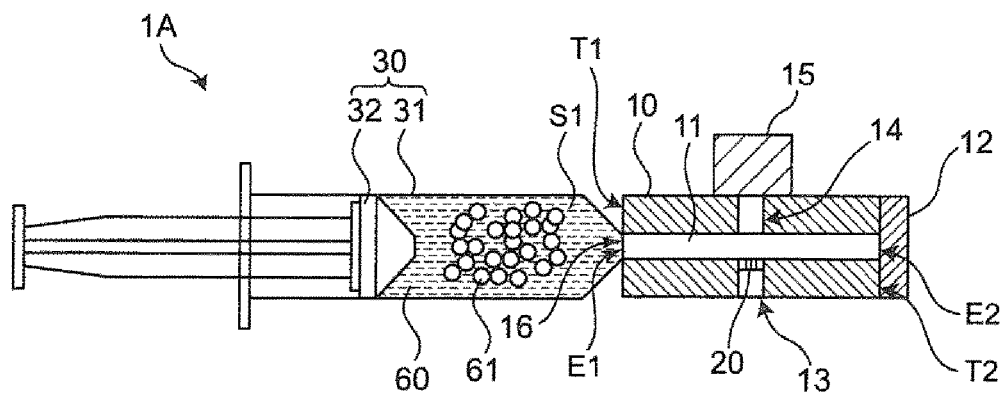
FIG. 6A illustrates an exemplary step in the filtration method according to Embodiment 1 of the present invention.

As illustrated in FIG. 5 and FIG. 6A, step ST11 involves providing the filtration device 1A in a state such that the liquid 60 including the target substance 61 is contained in the space S1 in the container 30.

For example, at step ST11, the liquid 60 including the target substance 61 is initially stored in a storage container (not shown) different from the container 30, and the liquid 60 including the target substance 61 is then transferred from the storage container into the space S1 in the container 30 before filtration is started. The movement of the liquid 60 from the storage container into the container 30 may be performed by, for example, changing the volume of the space S1 in the container 30 to suck in the liquid 60 contained in the storage container. Then, the container 30 containing the liquid 60 is attached to the attachment part 16 located at the one end T1 of the channel member 10. The filtration device 1A is thus provided in a state such that the liquid 60 including the target substance 61 is contained in the space S1 in the container 30.

Figure 6B:
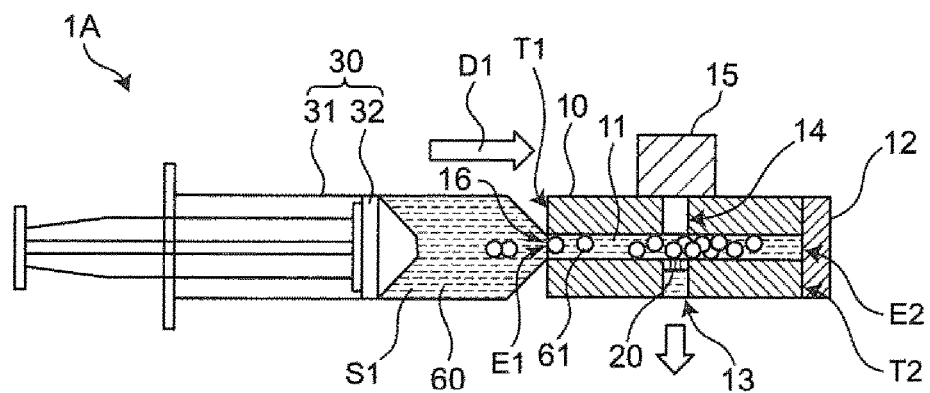
FIG. 6B illustrates an exemplary step in the filtration method according to Embodiment 1 of the present invention.

As illustrated in FIG. 5 and FIG. 6B, at step ST12, the volume of the space S1 in the container 30 is changed to allow supply of the liquid 60 contained in the container 30 to the channel 11 of the channel member 10. More specifically, the plunger 32 of the container 30 is pushed in a direction D1, which is a direction toward the distal end of the outer cylinder 31, thus decreasing the volume of the space S1 in the container 30. The liquid 60 contained in the container 30 is thus supplied to the channel 11 of the channel member 10.

Figure 6C:
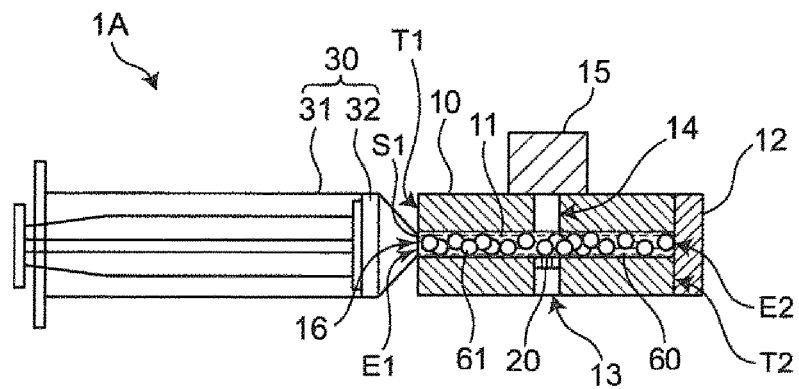
FIG. 6C illustrates an exemplary step in the filtration method according to Embodiment 1 of the present invention.

Step ST12 includes step ST13, which involves passing the liquid 60 through the filter 20. At step ST13, as the liquid 60 contained in the container 30 is supplied to the channel 11 of the channel member 10, the target substance 61 is trapped by the filter 20, and the liquid 60 passes through the filter 20. As illustrated in FIG. 6C, after filtration is completed, a volume of the liquid 60 including the target substance 61 equal to the volume of the channel 11 remains in the channel 11. By way of example, the volume of the channel 11 is 0.4 ml, and thus a very small volume, less than or equal to 0.4 ml, of the liquid 60 including the target substance 61 remains in the channel 11.

Figure 6D:
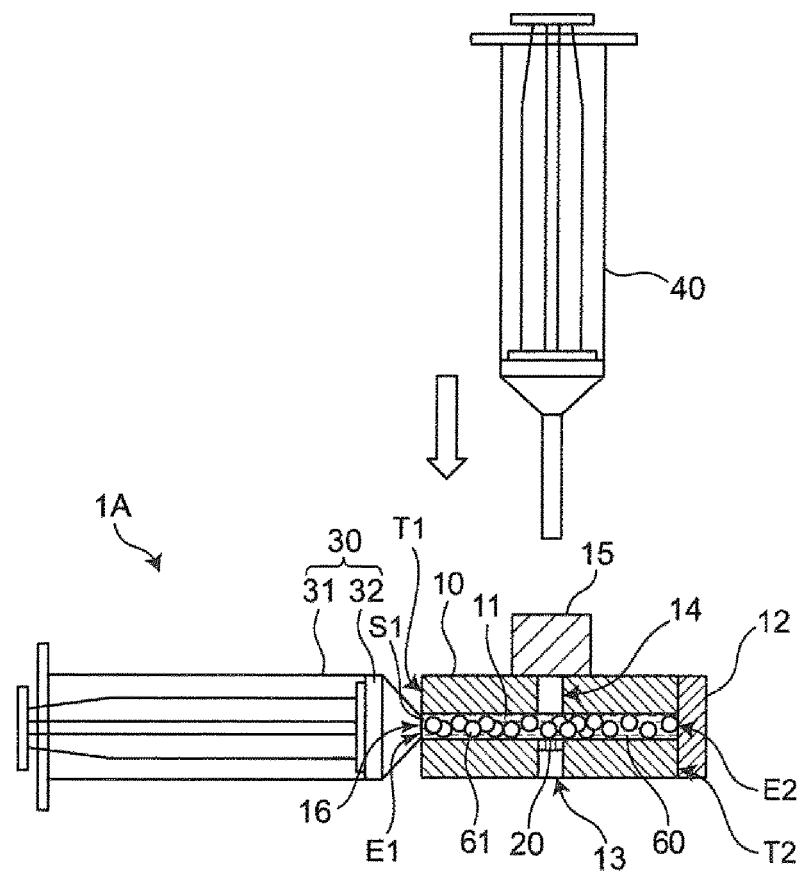
FIG. 6D illustrates an exemplary step in the filtration method according to Embodiment 1 of the present invention.

As illustrated in FIG. 5 and FIG. 6D, at step ST14, the target substance 61 in the channel 11 is collected by a collection device 40. The collection device 40 may be, for example, a syringe having an injection needle at its distal end.

Figure 6E:
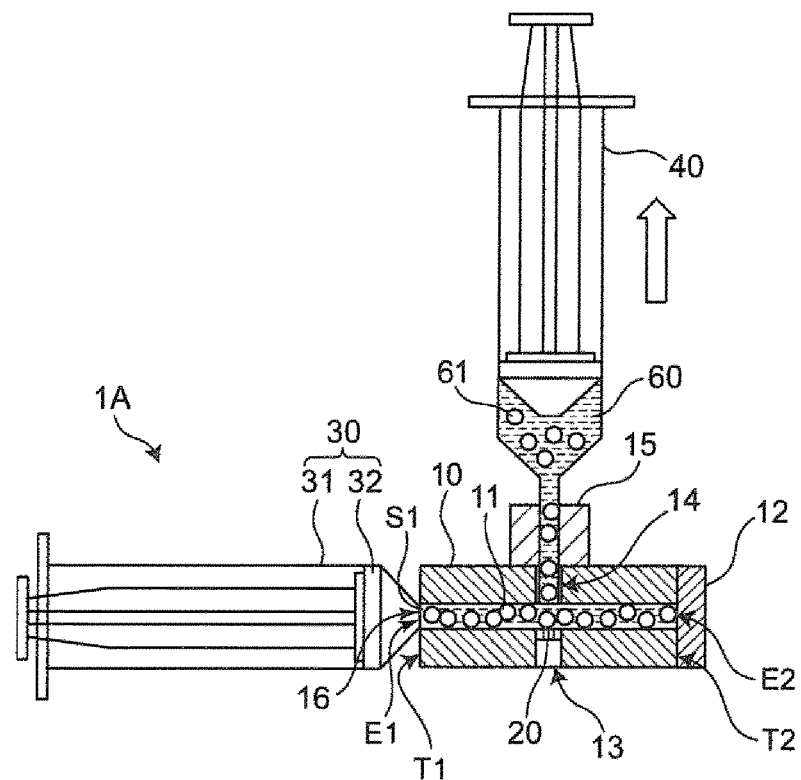
FIG. 6E illustrates an exemplary step in the filtration method according to Embodiment 1 of the present invention.

More specifically, at step ST14, the injection needle of the collection device 40 is penetrated through the cap 15 and its distal end is placed in the collection hole 14. Then, as illustrated in FIG. 6E, the plunger of the syringe serving as the collection device 40 is pulled to suck the target substance 61 remaining in the channel 11 of the channel member 10 into the collection device 40 together with the liquid 60. The liquid 60 including the target substance 61 and remaining in the channel 11 is thus collected.

Figure 6F:
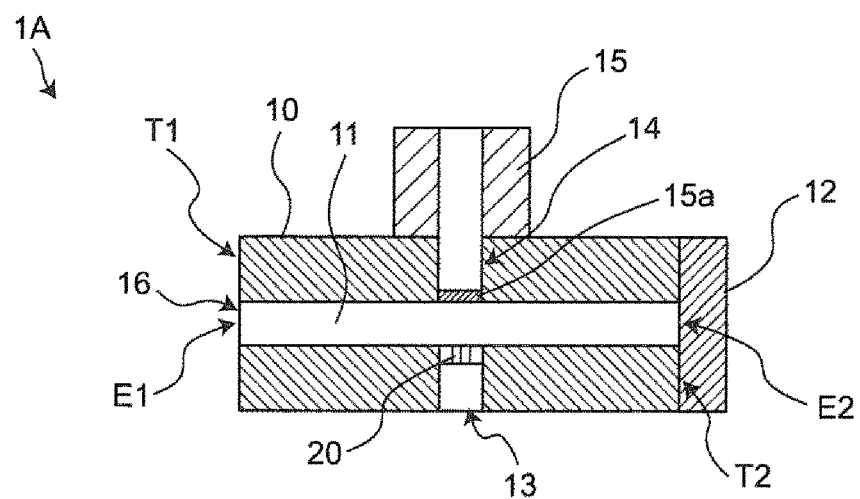
FIG. 6F is an enlarged illustration of an exemplary collection step in the filtration method according to Embodiment 1 of the present invention.
Figure 6G:
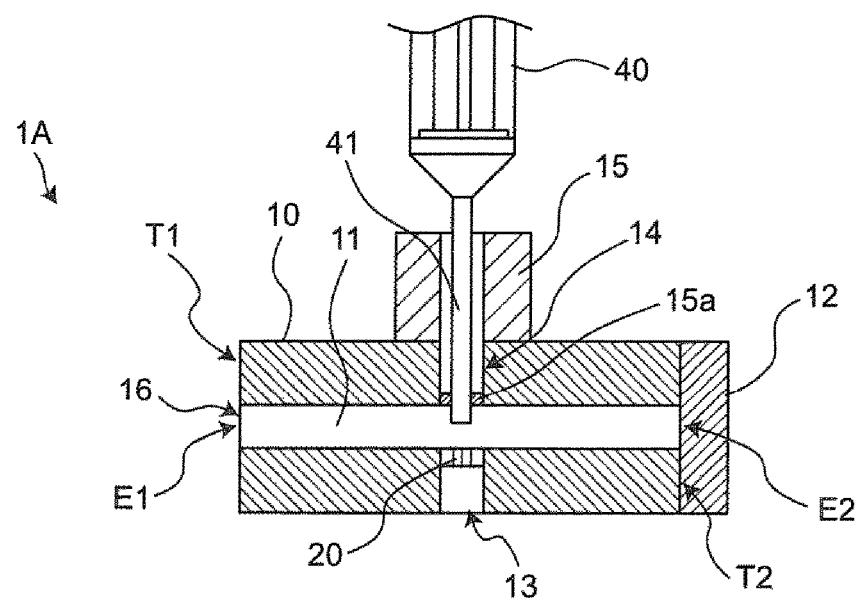
FIG. 6G is an enlarged illustration of an exemplary collection step in the filtration method according to Embodiment 1 of the present invention.

With reference to FIGS. 6F and 6G, the following describes an exemplary method for collecting a liquid including the target substance 61 by use of the collection device 40. FIGS. 6F and 6G each illustrate, in enlarged view, an exemplary collection step in a filtration method. In FIGS. 6F and 6G, the container 30, the target substance 61, and the liquid 60 are not depicted for the ease of illustration. As illustrated in FIG. 6F, the collection hole 14 is closed with a lid member 15a. The lid member 15a, which is attached inside the channel member 10, is located inside the collection hole 14. The lid member 15a may have a thickness of, for example, 10 μm to 1 mm. The lid member 15a is made of, for example, silicone rubber.

To collect the liquid 60 present in the channel 11 of the channel member 10, as illustrated in FIG. 6G, an injection needle 41 of the collection device 40 is penetrated through the lid member 15a. The distal end of the injection needle 41 is thus placed in the channel 11 of the channel member 10. Then, the liquid 60 including the target substance 61 and remaining in the channel 11 is sucked into the collection device 40 to thereby collect the liquid 60.

The filtration device 1A and the filtration method according to Embodiment 1 can provide the following advantageous effects.

The filtration device 1A includes the channel member 10, the filter 20 attached inside the channel member 10, and the container 30 attached to the channel member 10. The container 30 includes the space S1 of variable volume defined therein to contain the liquid 60 including the target substance 61. The channel member 10 includes the channel 11 and the opening 13 that are defined inside the channel member 10. The opening 13 is provided at a position along the channel 11 in a direction transverse to the direction in which the channel 11 extends. The channel member 10 also includes the attachment part 16 to which the container 30 is attached and which provides communication between the space S1 in the container 30 and the channel 11. The filter 20 is attached inside the channel member 10, and is positioned at the opening 13.

The above-mentioned configuration enables filtration of a desired volume of liquid. The filtration device 1A requires no piping to connect the container 30, which contains the liquid 60 including the target substance 61, with the channel member 10 to which the filter 20 is attached. This helps reduce the volume of the liquid 60 to be filtered. More specifically, the filtration device 1A enables filtration of very small liquid volumes, for example, less than or equal to 1 ml.

The filtration device 1A eliminates the need to use piping, a pump, and other components to form a circulating system, thus enabling filtration by use of a simple structure. Further, no piping is required between the container 30 and the channel member 10. This reduces the distance that the liquid 60 has to move from the container 30 to the channel 11 of the channel member 10, thus reducing damage to the target substance 61 due to such movement.

The filtration device 1A includes the space S1 of variable volume defined inside the container 30 to contain the liquid 60 including the target substance 61. This facilitates control of the volume of the liquid 60 to be filtered.

The channel member 10 of the filtration device 1A has the one end T1 and the other end T2. The one end T1 of the channel member 10 is provided with the attachment part 16 to which the container 30 is attached. The other end T2 of the channel member 10 is provided with the closing member 12. As a result, at the one end E1 of the channel 11 of the channel member 10, the attachment part 16 provides communication between the space S1 in the container 30 and the channel 11. The channel 11 of the channel member 10 is closed at the other end E2 with the closing member 12. This allows for easy passage of the liquid 60 through the filter 20 positioned at the opening 13.

With the filtration device 1A, a desired volume of the liquid 60 including the target substance 61 can be collected by designing the channel 11 of the channel member 10 to have a desired volume. In other words, the liquid 60 can be collected easily by designing the volume of the channel 11 of the channel member 10 based on the final volume of the liquid 60 including the target substance 61 that is desired to be collected. Further, the filtration device 1A enables filtration of very small liquid volumes less than or equal to, for example, 1 ml.

In the filtration device 1A, the opening 13, where the filter 20 is positioned, is provided in a direction transverse to the direction in which the channel 11 of the channel member 10 extends. This configuration allows the filter 20 to be placed along the flow of liquid supply from the container 30 to the channel 11. This makes it possible to reduce clogging of the filter 20.

In the filtration device 1A, the channel 11 of the channel member 10 is provided with the collection hole 14 to collect the target substance 61. This configuration helps ensure that, after filtration is finished, the target substance 61 in the channel 11 of the channel member 10 can be easily collected by the collection device 40.

The filtration device 1A preferably filters a cell as the target substance 61. Filtration with the filtration device 1A is performed by supplying the liquid 60 contained in the space S1 of variable volume in the container 30 to the channel 11 of the channel member 10 to pass the liquid 60 through the filter 20. The space S1 in the container 30 is closed except for the portion attached to the channel member 10, that is, its portion that communicates with the channel 11. The filtration device 1A thus enables filtration in a closed system. This makes the filtration device 1A less susceptible to intrusion of saprophytic bacteria or other bacteria, and contamination.

Cells are prone to deformation. In this regard, the filtration device 1A eliminates the need to use a pump or other such device to deliver the liquid 60 through piping, thus reducing pressure on the cells. This helps prevent cells from deforming and passing through the through-holes 23 of the filter 20, that is, prevent a decrease in recovery rate.

A filtration method using the filtration device 1A can also provide the same effects provided by the filtration device 1A mentioned above.

Although the foregoing description of Embodiment 1 is directed to the case where the filter 20 is a porous membrane made of metal, the invention is not so limited. The filter 20 may be any filter capable of separating the target substance 61 included in the liquid 60 from the liquid 60. For example, the filter 20 may be another filter such as a membrane filter.

Although the foregoing description of Embodiment 1 is directed to the case where the channel 11 has a circular cross-section, the invention is not so limited. The channel 11 may have, for example, a rectangular, elliptical, or semi-circular cross-section.

Although the foregoing description of Embodiment 1 is directed to the case where the channel member 10 and the closing member 12 are formed separately, the invention is not so limited. The channel member 10 and the closing member 12 may be formed integrally.

Although the foregoing description of Embodiment 1 is directed to the case where the opening 13 is provided inside the channel member 10 such that the opening 13 extends from the side wall of the middle portion of the channel 11 toward the bottom surface of the channel member 10, the invention is not so limited. The opening 13 may be provided anywhere as long as the opening 13 is connected to the channel 11. Likewise, although the collection hole 14 is provided inside the channel member 10 such that the collection hole 14 extends from the side wall of the middle portion of the channel 11 toward the top surface of the channel member 10, the collection hole 14 may not necessarily be provided at this position.

Although the foregoing description of Embodiment 1 is directed to the case where the container 30 is a syringe, the invention is not so limited. The container 30 may be any container including the space S1 of variable volume defined therein to contain the liquid 60 including the target substance 61. For example, any container 30 may be used as long as at least a portion of its inner wall in contact with the liquid 60 is movable. The container 30 may be any container whose movable inner wall is moved to allow supply of the liquid 60 to the channel 11 of the channel member 10. In Embodiment 1, a portion of the plunger 32 of the syringe (container 30) illustrated in FIGS. 6A to 6E in contact with the liquid 60 corresponds to the movable inner wall of the container 30.

Figure 7:
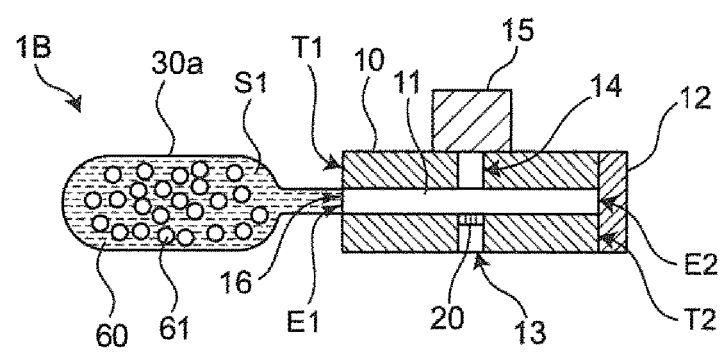
FIG. 7 is a schematic diagram of a filtration device according to a modification of Embodiment 1 of the present invention.

FIG. 7 is a schematic diagram of a filtration device 1B according to a modification of Embodiment 1 of the present invention. As illustrated in FIG. 7, the filtration device 1B may include a container 30a in the form of a flexible pouch. With the filtration device 1B, the container 30a is deformed to move at least a portion of the inner wall of the container 30a. The liquid 60 contained in the space S1 in the container 30a is thus supplied to the channel 11 of the channel member 10. This configuration allows the liquid 60 in the container 30a to be supplied to the channel 11 of the channel member 10 for filtration.

Although the foregoing description of Embodiment 1 is directed to the case where the collection device 40 is used to collect the target substance 61 remaining in the channel 11 of the channel member 10, the invention is not so limited. For example, another configuration may involve, after filtration is finished, removing the cap 15, and pulling the plunger 32 of the container 30 to collect the target substance 61 remaining in the channel 11 of the channel member 10 together with a very small volume of the liquid 60.

Although the foregoing description of Embodiment 1 is directed to the case where the target substance 61 is a cell, the invention is not so limited. The target substance 61 may be any substance desired to be separated from the liquid 60.

Embodiment 2

A filtration device according to Embodiment 2 of the present invention will be described below.

The following description of Embodiment 2 will mainly focus on differences from Embodiment 1. In the following description of Embodiment 2, features identical or equivalent to those in Embodiment 1 will be designated by the same reference signs. In Embodiment 2, features overlapping those of Embodiment 1 will not be described in repetitive detail.

Figure 8:
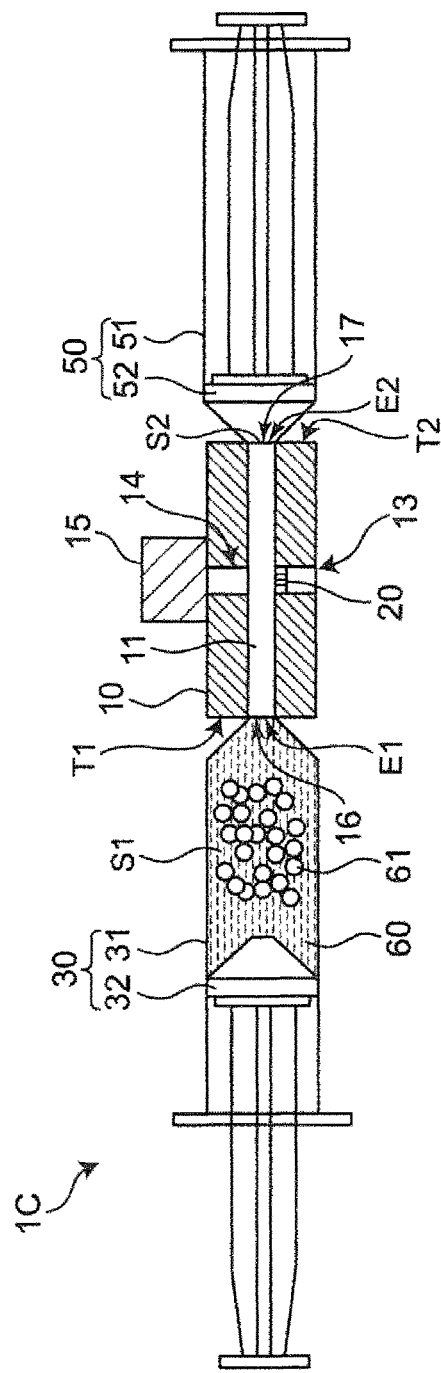
FIG. 8 is a schematic diagram of a filtration device according to Embodiment 2 of the present invention.

FIG. 8 is a schematic diagram of a filtration device 1C according to Embodiment 2 of the present invention. As illustrated in FIG. 8, Embodiment 2 differs from Embodiment 1 in that a container 50 is attached to the other end T2 of the channel member 10.

In Embodiment 2, the container 30 attached to the one end T1 of the channel member 10 is defined as a first container 30, the space S1 in the first container 30 is defined as a first space S1, and the attachment part 16 is defined as a first attachment part 16. The container 50 attached to the other end T2 of the channel member 10 is defined as a second container 50.

The second container 50 is used to contain the liquid 60 including the target substance 61. A second space S2 (see, e.g., FIG. 10B) of variable volume is defined in the second container 50 to contain the liquid 60 including the target substance 61 that has moved to the second space S2 from the first space S1 in the first container 30 via the channel 11. In Embodiment 2, the volume of the second space S2 in the second container 50 is variable from, for example, 0 to 5 ml.

In Embodiment 2, as with the first container 30, the second container 50 is a syringe. More specifically, the second container 50 includes an outer cylinder 51, and a plunger 52 that is movable within the outer cylinder 51. A gasket is attached at the distal end of the plunger 52.

In the second container 50, the inside of the outer cylinder 51, and the plunger 52 define the second space S2 of variable volume. For example, for the second container 50, the second space S2 in the outer cylinder 51 can be decreased in volume by pushing the plunger 52 disposed inside the outer cylinder 51. The liquid 60 contained in the second space S2 in the second container 50 can be thus supplied to the channel 11 of the channel member 10. For the second container 50, the second space S2 in the outer cylinder 51 can be increased in volume by pulling the plunger 52 disposed inside the outer cylinder 51. This allows the second space S2 in the second container 50 to contain the liquid 60 that has moved to the second space S2 from the first space S1 in the first container 30 via the channel 11.

In Embodiment 2, the other end T2 of the channel member 10 is provided with a second attachment part 17 to which the second container 50 is attached and which provides communication between the second space S2 in the second container 50 and the channel 11 of the channel member 10. The second attachment part 17 is similar in configuration to the first attachment part 16 and thus will not be described in further detail.

With the filtration device 1C, cross-flow filtration is performed by moving the liquid 60 including the target substance 61 from the first container 30 to the second container 50 via the channel 11 of the channel member 10, and moving the liquid 60 from the second container 50 to the first container 30 via the channel 11 of the channel member 10.

Figure 9:
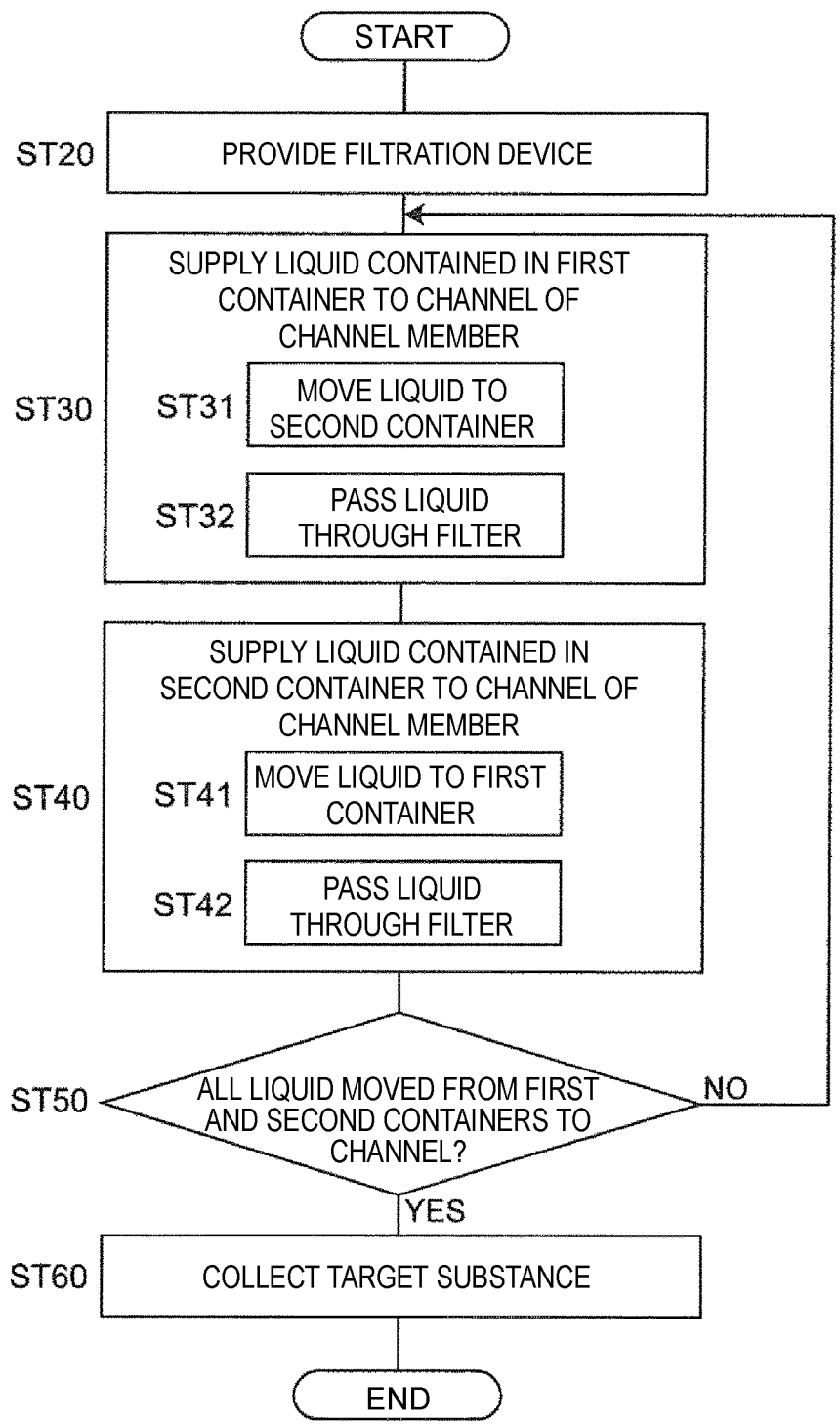
FIG. 9 is an exemplary flowchart of a filtration method according to Embodiment 2 of the present invention.

A filtration method using the filtration device 1C will be described below with reference to FIG. 9 and FIGS. 10A to 10G. FIG. 9 is an exemplary flowchart of a filtration method according to Embodiment 2 of the present invention. FIGS. 10A to 10G each illustrate an exemplary step in the filtration method according to Embodiment 2 of the present invention.

As illustrated in FIG. 9 and FIG. 10A, step ST20 involves providing the filtration device 1C. More specifically, step ST20 involves providing the filtration device 1C in a state such that the liquid 60 including the target substance 61 is contained in the first space S1 in the first container 30. In the second container 50, the gasket at the distal end of the plunger 52 is placed at the other end E2 of the channel 11. In other words, the second space S2 in the second container 50 is adjusted to its smallest volume.

As illustrated in FIG. 9 and FIG. 10B, at step ST30, the volume of the first space S1 in the first container 30 is changed to allow the liquid 60 in the first container 30 to be supplied to the channel 11 of the channel member 10. More specifically, the plunger 32 of the first container 30 is pushed in a direction D2, which is a direction toward the distal end of the outer cylinder 31, thus decreasing the volume of the first space S1 in the first container 30. The liquid 60 contained in the first container 30 is thus supplied to the channel 11 of the channel member 10.

Step ST30 includes step ST31, which involves moving the liquid 60 contained in the first container 30 to the second container 50 via the channel 11 of the channel member 10. At step ST31, the plunger 52 of the second container 50 is pulled in a direction D3, which is a direction away from the distal end of the outer cylinder 51, thus increasing the volume of the second space S2 in the second container 50. The liquid 60 from the first container 30 thus moves into the second container 50 via the channel 11 of the channel member 10.

Step ST30 also includes step ST32, which involves passing the liquid 60 through the filter 20. At step ST32, as the liquid 60 contained in the first container 30 is supplied to the channel 11 of the channel member 10, the target substance 61 is trapped by the filter 20, and a portion of the liquid 60 flowing in the channel 11 passes through the filter 20.

Step ST30 is continued until all of the liquid 60 in the first container 30 is supplied to the channel 11 of the channel member 10 and to the second container 50 as illustrated in FIG. 10C.

As described above, at step ST30, the liquid 60 including the target substance 61 is moved from the first container 30 toward the second container 50 through the channel 11, and a portion of the liquid 60 is passed through the filter 20. Cross-flow filtration is thus performed at step ST30.

Figure 10D:
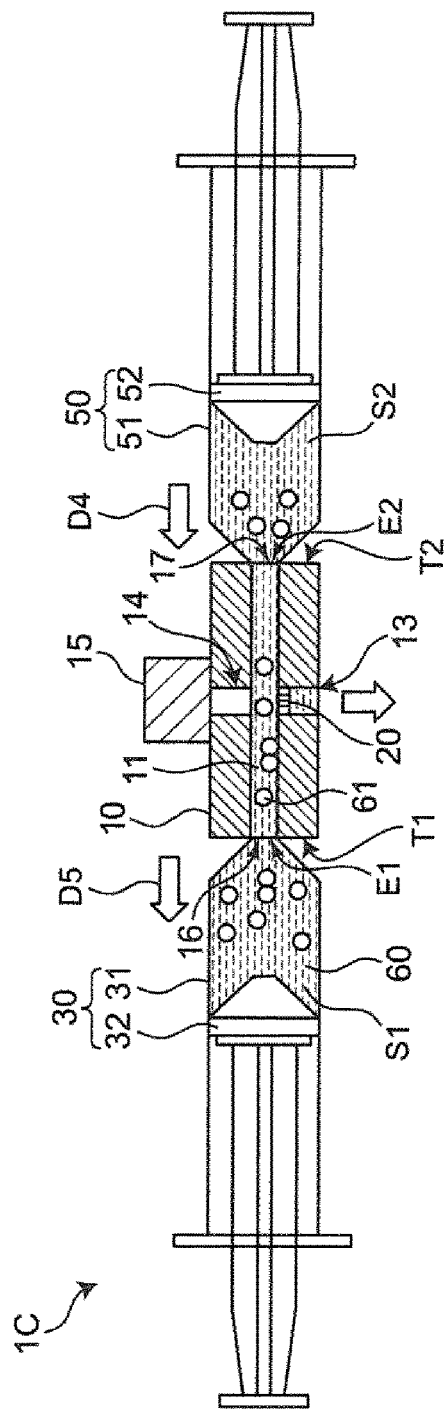
FIG. 10D illustrates an exemplary step in the filtration method according to Embodiment 2 of the present invention.

Then, as illustrated in FIG. 9 and FIG. 10D, at step ST40, the volume of the second space S2 in the second container 50 is changed to allow supply of the liquid 60 contained in the second container 50 to the channel 11 of the channel member 10. More specifically, the plunger 52 of the second container 50 is pushed in a direction D4, which is a direction toward the distal end of the outer cylinder 51, thus decreasing the volume of the second space S2 in the second container 50. The liquid 60 contained in the second container 50 is thus supplied to the channel 11 of the channel member 10.

Step ST40 includes step ST41, which involves moving the liquid 60 contained in the second container 50 to the first container 30 via the channel 11 of the channel member 10. At step ST41, the plunger 32 of the first container 30 is pulled in a direction D5, which is a direction away from the distal end of the outer cylinder 31, thus increasing the volume of the first space S1 in the first container 30. The liquid 60 from the second container 50 thus moves into the first container 30 via the channel 11 of the channel member 10.

Step ST40 includes step ST42, which involves passing the liquid 60 through the filter 20. At step ST42, as the liquid 60 contained in the second container 50 is supplied to the channel 11 of the channel member 10, the target substance 61 is trapped by the filter 20, and a portion of the liquid 60 flowing in the channel 11 passes through the filter 20.

Step ST40 is continued until all of the liquid 60 in the second container 50 is supplied to the channel 11 of the channel member 10 and to the first container 30.

As described above, at step ST40, the liquid 60 including the target substance 61 is moved from the second container 50 toward the first container 30 through the channel 11, and a portion of the liquid 60 is passed through the filter 20.

As illustrated in FIG. 9 and FIG. 10E, at step ST50, step ST30 and step ST40 are repeated until all of the liquid 60 moves from the first container 30 and the second container 50 to the channel 11 of the channel member 10.

Figure 10F:
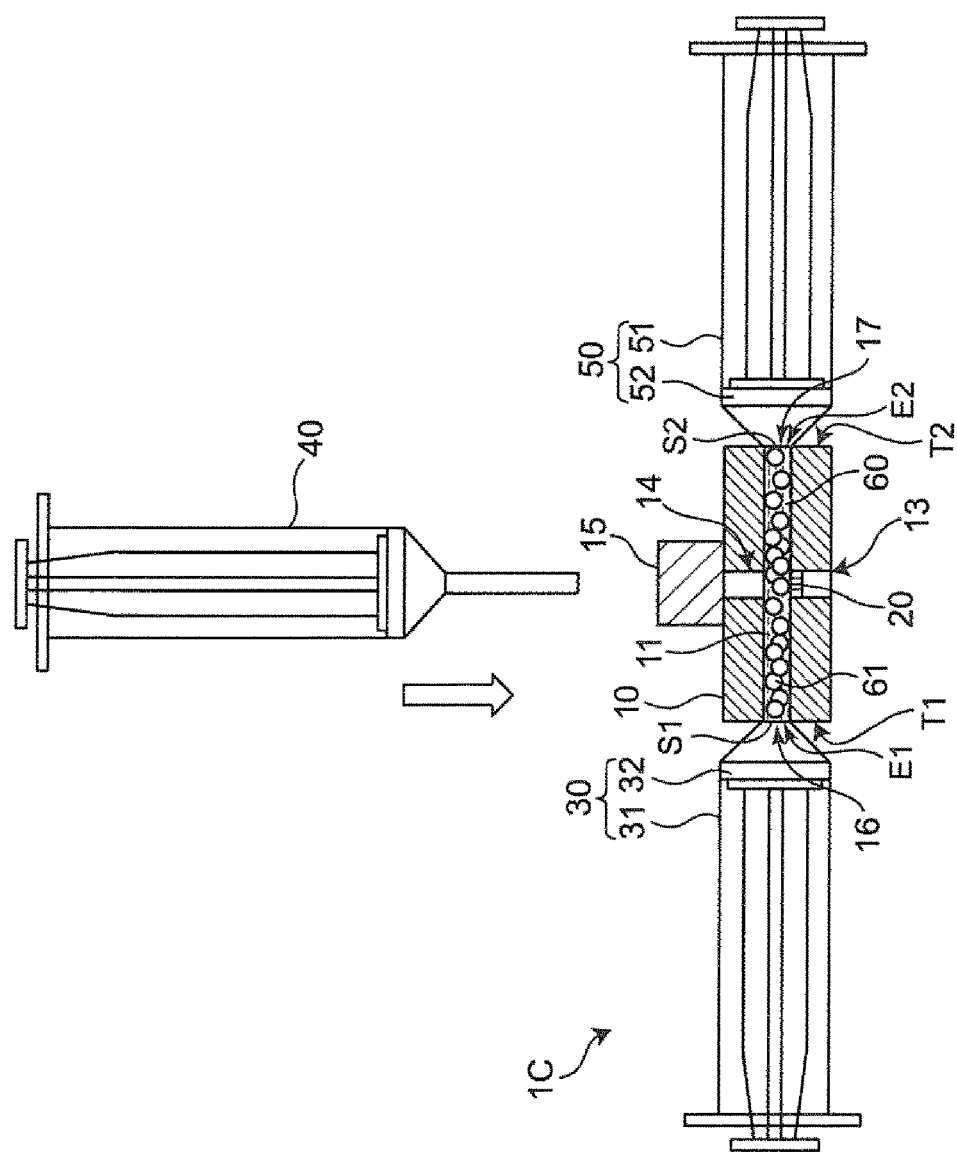
FIG. 10F illustrates an exemplary step in the filtration method according to Embodiment 2 of the present invention.
Figure 10G:
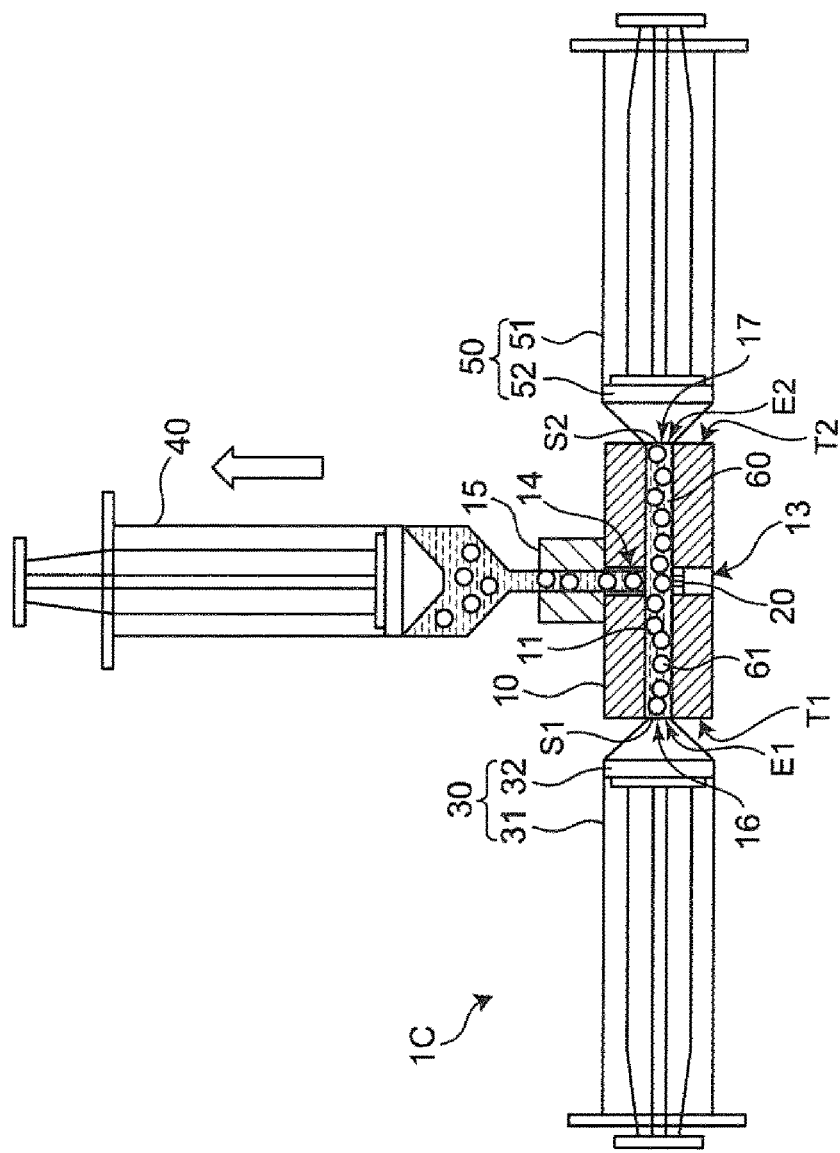
FIG. 10G illustrates an exemplary step in the filtration method according to Embodiment 2 of the present invention.

As illustrated in FIG. 9 and FIGS. 10F and 10G, at step ST60, the target substance 61 in the channel 11 is collected by the collection device 40 in the same manner as with step ST14 according to Embodiment 1.

The filtration device 1C and the filtration method according to Embodiment 2 can provide the following effects.

The filtration device 1C includes the first container 30 attached to the one end T1 of the channel member 10, and the second container 50 attached to the other end T2 of the channel member 10. The first container 30 includes the first space S1 of variable volume defined therein to contain the liquid 60 including the target substance 61. The second container 50 includes the second space S2 of variable volume defined therein to contain the liquid 60 including the target substance 61.

The above-mentioned configuration makes it possible to move the liquid 60 including the target substance 61 from the first container 30 to the second container 50 via the channel 11 of the channel member 10, and move the liquid 60 including the target substance 61 from the second container 50 to the first container 30 via the channel 11 of the channel member 10. Further, as the liquid 60 passes through the channel 11 of the channel member 10, a portion of the liquid 60 can be filtered through the filter 20 positioned at the opening 13.

As described above, the filtration device 1C enables cross-flow filtration of the liquid 60 including the target substance 61 by the filter 20 while causing the liquid 60 to reciprocate between the first container 30 and the second container 50 via the channel 11 of the channel member 10.

The filtration device 1C causes the liquid 60 to reciprocate a plurality of times between the first container 30 and the second container 50 via the channel 11 of the channel member 10 until all of the liquid 60 moves to the channel 11 from the first space S1 in the first container 30 and from the second space S2 in the second container 50. This configuration helps reduce pressure on the target substance 61 in comparison to Embodiment 1.

Although the foregoing description of Embodiment 2 is directed to the case where each of the first container 30 and the second container 50 is a syringe, the invention is not so limited.

FIG. 11 is a schematic diagram of a filtration device 1D according to a modification of Embodiment 2 of the present invention. As illustrated in FIG. 11, the filtration device 1D may include the first container 30 in the form of a syringe, and a second container 50a in the form of a flexible pouch. With the filtration device 1D, pushing the plunger 32 of the first container 30 causes the liquid 60 to move to the second container 50a via the channel 11 of the channel member 10. The second space S2 in the second container 50a expands due to the pressure exerted by the liquid 60 moving toward the second container 50a from the first container 30. Then, the plunger 32 of the first container 30 is pulled, thus causing the liquid 60 to move from the second container 50a to the first container 30 via the channel 11. With the above-mentioned configuration, changing the volume of the first space S1 in the first container 30 thus allows the volume of the second space S2 in the second container 50a to change in a synchronized fashion. This facilitates filtration.

Figure 12:
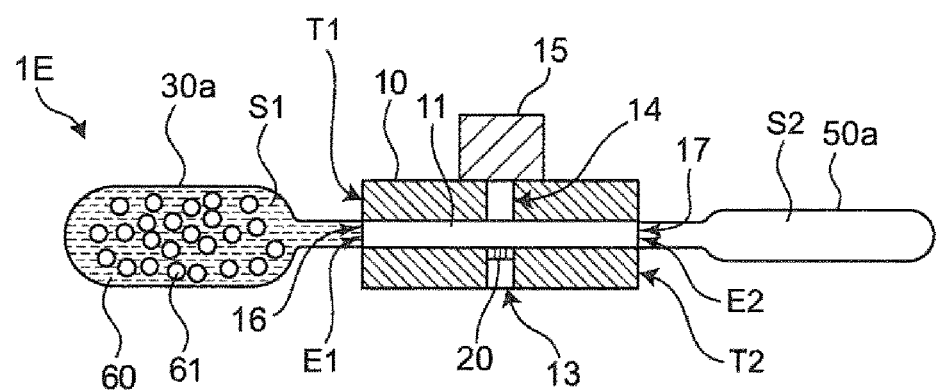
FIG. 12 is a schematic diagram of a filtration device according to another modification of Embodiment 2 of the present invention.

FIG. 12 is a schematic diagram of a filtration device 1E according to another modification of Embodiment 2 of the present invention. As illustrated in FIG. 12, the filtration device 1E may include a first container 30a and the second container 50a that are each formed as a flexible pouch. The filtration device 1E can provide the same effects as the filtration device 1D.

Although the foregoing description of Embodiment 2 is directed to the case where step ST30 and step ST40 are repeated at step ST50 until all of the liquid 60 moves to the channel 11 from the first space S1 in the first container 30 and from the second space S2 in the second container 50, the invention is not so limited. For example, at step ST50, filtration may be finished with the liquid 60 remaining in the first container 30 and the second container 50.

Example 1

A filtration experiment was carried out under the conditions below by using the filtration device 1C according to Embodiment 2.

Liquid volume: 5 ml (including 5×104 cells)
Initial concentration: 1×104 cells/ml
Target solution volume: 0.3 ml or less
Pressing force on the syringe: about 1.6 N
Cell type: HL-60
Culture solution: RPMI1640 (L-glutamine-containing) culture medium (a culture solution with 10 vol % of fetal bovine serum and 1 vol % of penicillin-streptomycin)

In Example 1, movement of the liquid 60 from the first space S1 in the first container 30 to the second space S2 in the second container 50, and movement of the liquid 60 from the second space S2 in the second container 50 to the first space S1 in the first container 30 were each counted as one movement, and the number of such movements of the liquid 60 was counted.

In Example 1, on the 27th movement of the liquid 60, all of the liquid 60 in the first container 30 and the second container 50 moved to the channel 11 of the channel member 10, and 0.3 ml or less of the liquid 60 including the target substance 61 was successfully collected.

Embodiment 3

A filtration device according to Embodiment 3 of the present invention will be described below.

The following description of Embodiment 3 will mainly focus on differences from Embodiment 2. In the following description of Embodiment 3, features identical or equivalent to those in Embodiment 2 will be designated by the same reference signs. In Embodiment 3, features overlapping those of Embodiment 2 will not be described in repetitive detail.

Figure 13:
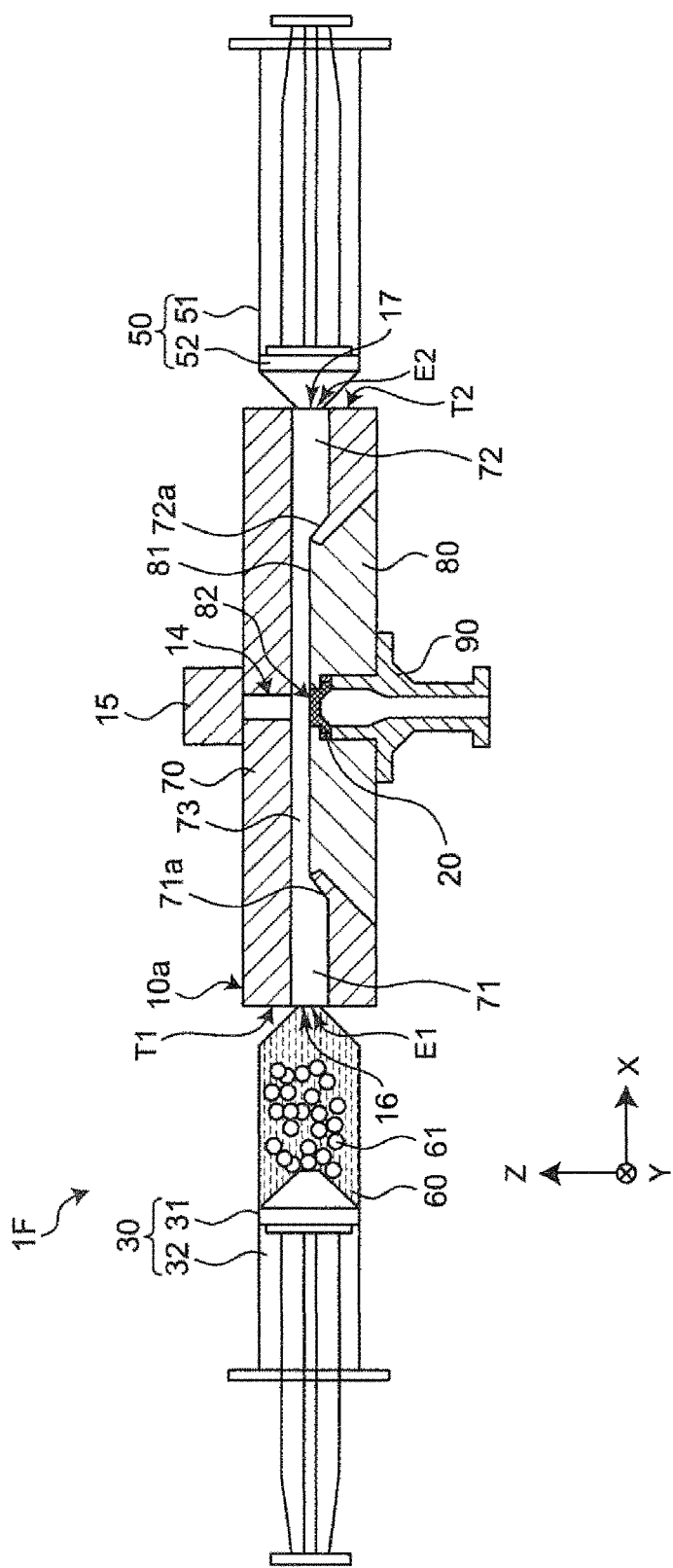
FIG. 13 is a schematic diagram of a filtration device according to Embodiment 3 of the present invention.

FIG. 13 is a schematic diagram of a filtration device 1F according to Embodiment 3 of the present invention. As illustrated in FIG. 13, Embodiment 3 differs from Embodiment 2 in that a channel 73, which is provided inside a channel member 10a and at which the filter 20 is positioned, has a smaller cross-sectional area than other channels 71 and 72.

In Embodiment 3, the channel member 10a includes first and second channel members 70 and 80 which detachably mate with each other. The filter 20 is held by a holder 90 to attach the filter 20 inside the second channel member 80 such that the filter 20 is positioned at an opening 82 defined in a projecting surface 81 of the second channel member 80.

The first container 30 is attached to one end T1 of the channel member 10a via the first attachment part 16. The second container 50 is attached to the other end T2 of the channel member 10a via the second attachment part 17.

The channel member 10a includes a first channel 71, a second channel 72, and a third channel 73 that are defined therein. The first channel 71 communicates with the first space S1 in the first container 30. The second channel 72 communicates with the second space S2 of the second container 50. The third channel 73, at which the filter 20 is positioned, is provided between the first channel 71 and the second channel 72. The first channel 71 and the third channel 73 are connected via a first connection part 71a. The second channel 72 and the third channel 73 are connected via a second connection part 72a.

The third channel 73, which corresponds to the filtration portion, has a smaller cross-sectional area than the first and second channels 71 and 72. In Embodiment 3, the first channel 71 and the second channel 72 have the same cross-sectional area. The term cross-sectional area as used herein refers to the cross-sectional area of a channel taken along a direction orthogonal to the direction in which the channel extends. The channel member 10a will be described in more detail below.

Figure 14A:
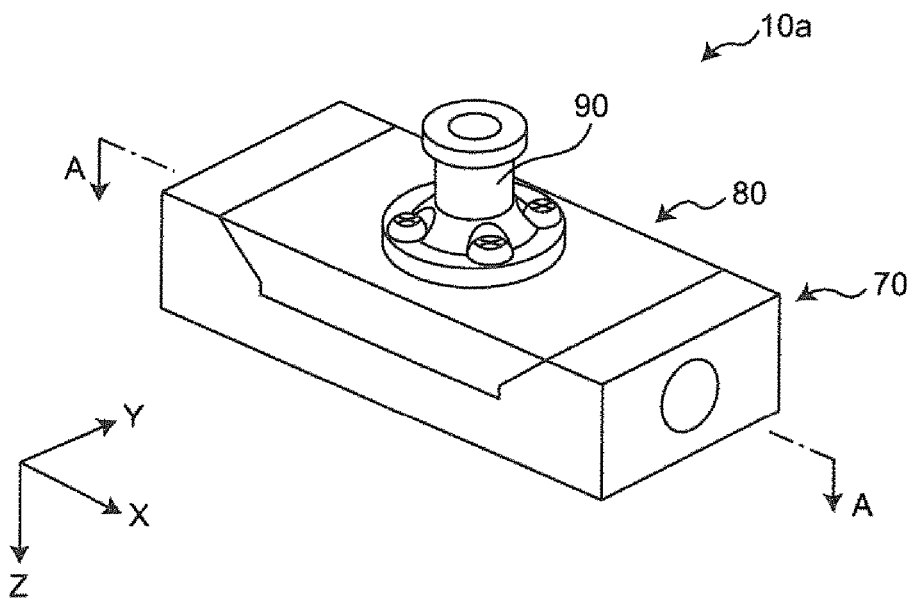
FIG. 14A is a schematic perspective view of a channel member according to Embodiment 3 of the present invention.
Figure 14B:
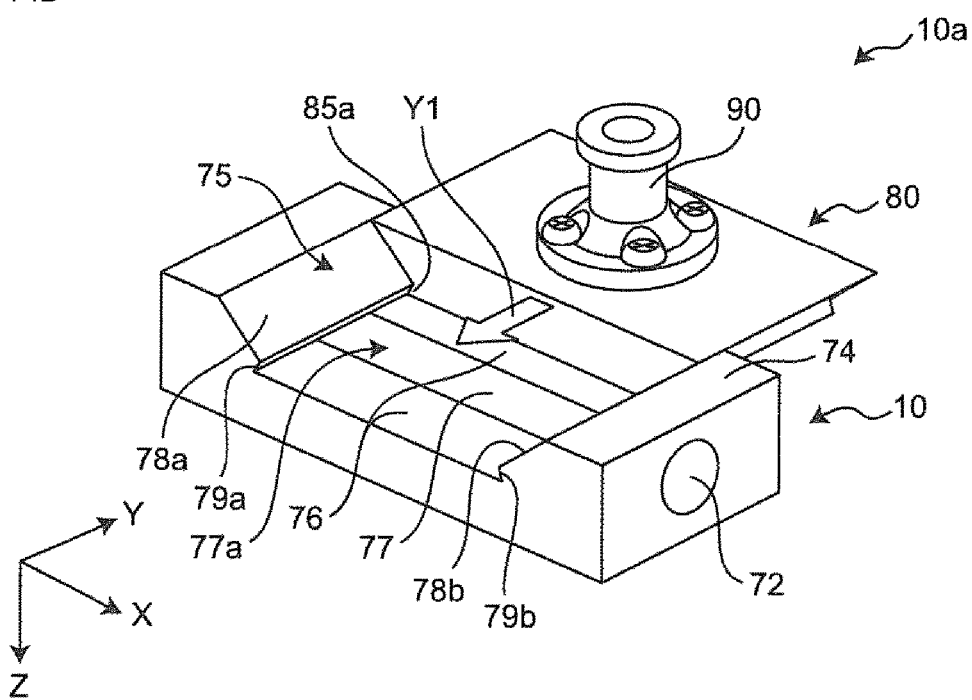
FIG. 14B is a perspective view of the channel member according to Embodiment 3 of the present invention, illustrating an example of how a second channel member is attached to a first channel member.
Figure 15:
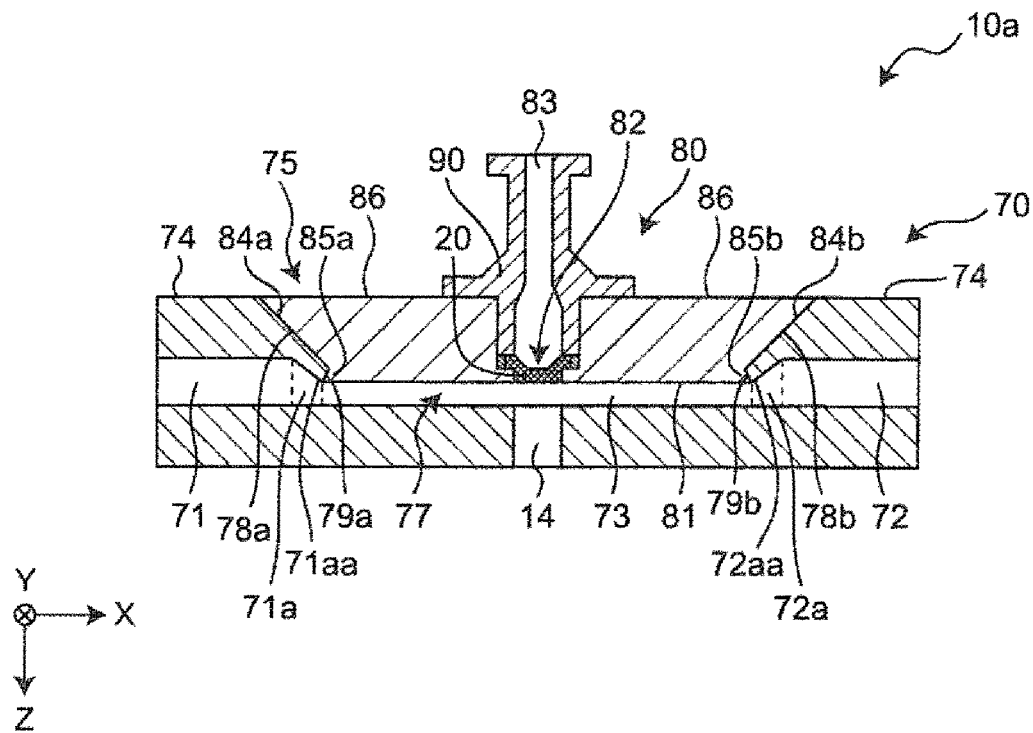
FIG. 15 is a cross-section taken along a line A-A in FIG. 14A.

FIG. 14A is a schematic perspective view of the channel member 10a according to Embodiment 3 of the present invention. FIG. 14B is a schematic perspective view of the channel member 10a, illustrating how the second channel member 80 is attached to the first channel member 70 in the filtration device 1F. FIG. 15 is a cross-section taken along a line A-A in FIG. 14A. In FIGS. 14A and 14B and FIG. 15, the channel member 10a illustrated in FIG. 13 is depicted upside down for ease of description.

As illustrated in FIG. 14A and FIG. 15, the filtration device 1F includes the first channel member 70, the second channel member 80 that detachably mates with the first channel member 70, and the filter 20 attached to the second channel member 80. In Embodiment 3, the filter 20 is attached to the second channel member 80 by fastening the holder 90 with a screw or other such fastening component.

As illustrated in FIG. 14B, in Embodiment 3, the second channel member 80 is attached to the first channel member 70 by sliding the second channel member 80 in a Y1 direction relative to the first channel member 70.

As illustrated in FIG. 15, the filtration device 1F is provided with the first channel 71, the second channel 72, and the third channel 73. The first channel 71 and the second channel 72 are each defined by a through-hole. The first channel 71 and the third channel 73 are connected via the first connection part 71a. The second channel 72 and the third channel 73 are connected via the second connection part 72a. The third channel 73, which corresponds to the filtration portion, has a smaller cross-sectional area than the first and second channels 71 and 72.

Figure 16A:
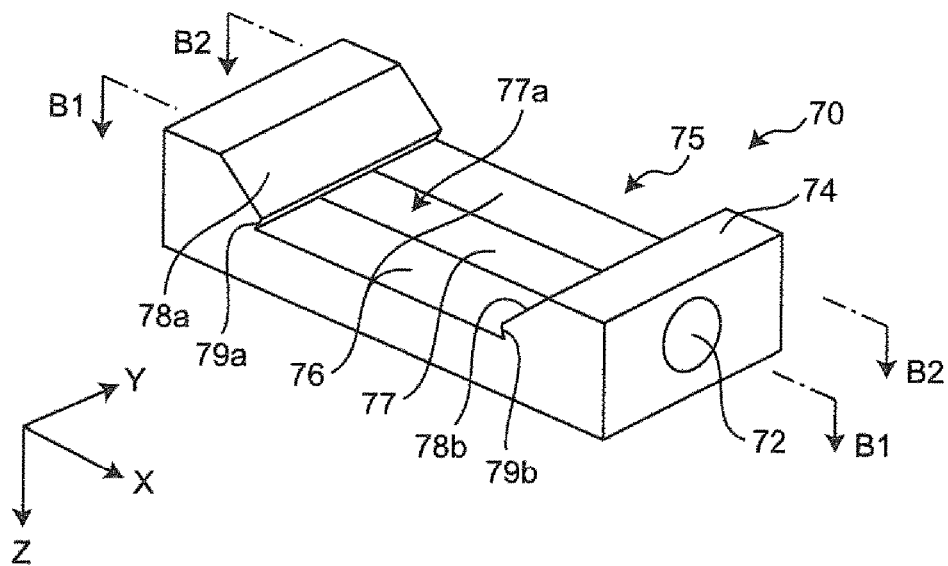
FIG. 16A is a schematic perspective view of the first channel member of the channel member according to Embodiment 3 of the present invention.
Figure 16B:
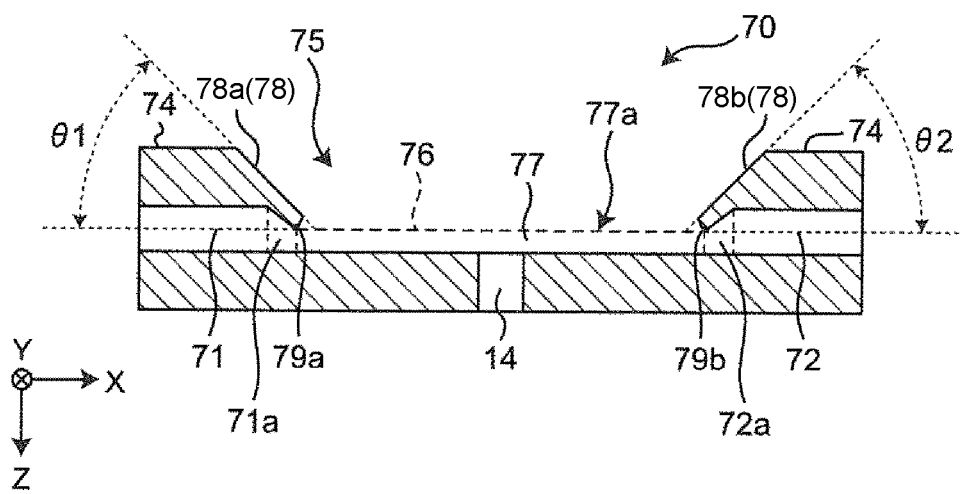
FIG. 16B is a cross-section taken along a line B1-B1 in FIG. 16A.
Figure 16C:
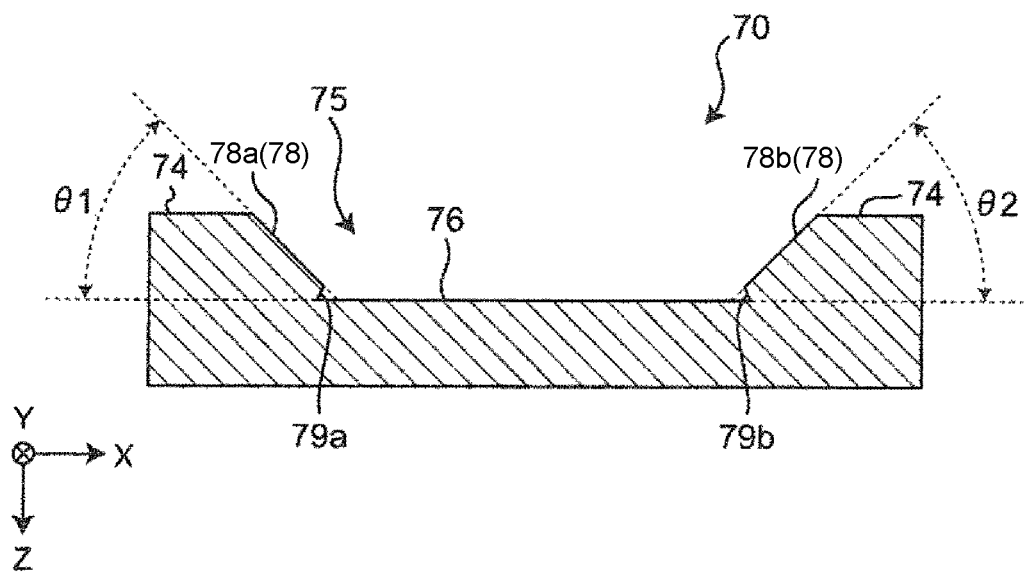
FIG. 16C is a cross-section taken along a line B2-B2 in FIG. 16A.

FIG. 16A is a schematic perspective view of the first channel member 70 of the filtration device 1F according to Embodiment 3 of the present invention. FIG. 16B is a cross-section taken along a line B1-B1 in FIG. 16A. FIG. 16C is a cross-section taken along a line B2-B2 in FIG. 16A. In FIGS. 16A, 16B, and 16C, the first channel member 70 illustrated in FIG. 13 is depicted upside down for ease of description.

As illustrated in FIGS. 16A to 16C, the first channel member 70 has a recess 75, a groove 77, and the first and second channels 71 and 72. The recess 75 is recessed inward from a first outer wall surface 74. The groove 77 has an opening 77a in a recessed surface 76 of the recess 75. The first and second channels 71 and 72 are each defined by a through-hole connected to the groove 77. The first channel member 70 also has the first connection part 71a that connects the groove 77 with the first channel 71, and the second connection part 72a that connects the groove 77 with the second channel 72. More specifically, the first channel member 70 has the recess 75 that is recessed inward (+Z direction) from the first outer wall surface 74, which is a flat surface, and also includes the first and second channels 71 and 72 defined therein. The outer wall surface of the first channel member 70 opposite to the first outer wall surface 74 is parallel to the first outer wall surface 74. The first channel 71 extends in the −X direction, and the second channel 72 extends in the +X direction. This configuration helps reduce the height (length in the Z direction) of the first channel member 70. The first and second channels 71 and 72 are formed in the shape of a circular tube.

The recessed surface 76 of the recess 75 of the first channel member 70 defines a flat surface. The recessed surface 76 of the recess 75 is provided with the groove 77 connected to the first and second channels 71 and 72. The groove 77 has a recessed configuration. The groove 77 has the opening 77a in the recessed surface 76 of the recess 75. The groove 77 is formed linearly. In Embodiment 3, the groove 77 has a semi-circular cross-section when taken in the Y direction. The groove 77 extends linearly in the X direction.

The first channel 71 and the second channel 72 are connected to the groove 77. The first channel 71 is connected to the groove 77 via the first connection part 71a. The second channel 72 is connected to the groove 77 via the second connection part 72a. In the first connection part 71a between the first channel 71 and the groove 77, and in the second connection part 72a between the second channel 72 and the groove 77, the first and second channels 71 and 72 decrease in cross-sectional area with increasing proximity to the groove 77. More specifically, the first connection part 71a defines a first connection slope 71aa that connects the first channel 71 with one end of the groove 77. The second connection part 72a defines a second connection slope 72aa that connects the second channel 72 with the other end of the groove 77. The first connection slope 71aa is inclined so as to narrow the first channel 71. The second connection slope 72aa is inclined so as to enlarge the groove 77.

The first channel member 70 has a recessed mating surface 78 on the lateral side of the recess 75 to allow mating between the recess 75 and a projection 87 described later. The recessed mating surface 78 defines a slope inclined with respect to the recessed surface 76 of the recess 75. In Embodiment 3, the recessed mating surface 78 includes a first slope 78a, and a second slope 78b. The angle θ1 formed by the first slope 78a and the recessed surface 76, and the angle θ2 formed by the second slope 78b and the recessed surface 76 are, for example, 45 degrees.

As illustrated in FIGS. 16B and 16C, the recessed mating surface 78 includes notches 79a and 79b recessed inwardly of the first channel member 70. More specifically, the first slope 78a includes, in its end portion adjacent to the recessed surface 76, a first notch 79a notched in a direction in which the first channel 71 extends (−X direction). The second slope 78b includes, in its end portion adjacent to the recessed surface 76, a second notch 79b where the second slope 78b is notched in a direction (+X direction) in which the second channel 72 extends. The first notch 79a is inclined with respect to the Z-axis by, for example, two degrees in the +X direction, and the second notch 79b is inclined with respect to the Z-axis by, for example, two degrees in the −X direction.

The lateral side of the recess 75 transverse to the third channel 73 is open. In Embodiment 3, the lateral side of the recess 75 in a direction (Y direction) orthogonal to the third channel 73 is open. Thus, as illustrated in FIG. 14B, in mating the first channel member 70 and the second channel member 80 with each other, the second channel member 80 can be inserted into the first channel member 70 from the open lateral side of the recess 75 by sliding the second channel member 80 in a direction (Y1 direction) transverse (e.g., orthogonal) to the direction (X direction) in which the groove 77 extends. At this time, as illustrated in FIG. 15, the second channel member 80 slides relative to the first channel member 70 in a state in which first and second protrusions 85a and 85b of the second channel member 80, which will be described later, are respectively mated with the first and second notches 79a and 79b. By sliding the second channel member 80 relative to the first channel member 70, the second channel member 80 can be easily attached to or detached from the first channel member 70. It is to be noted that the first notch 79a and the second notch 79b are depicted in exaggerated form in the drawings.

The first channel member 70 is made of, for example, polymethyl methacrylate (PMMA), or polystyrene (PS), or polyphenylene sulfide (PPS).

In Embodiment 3, the collection hole 14 is provided in the first channel member 70, and connects to the third channel 73.

Figure 17A:
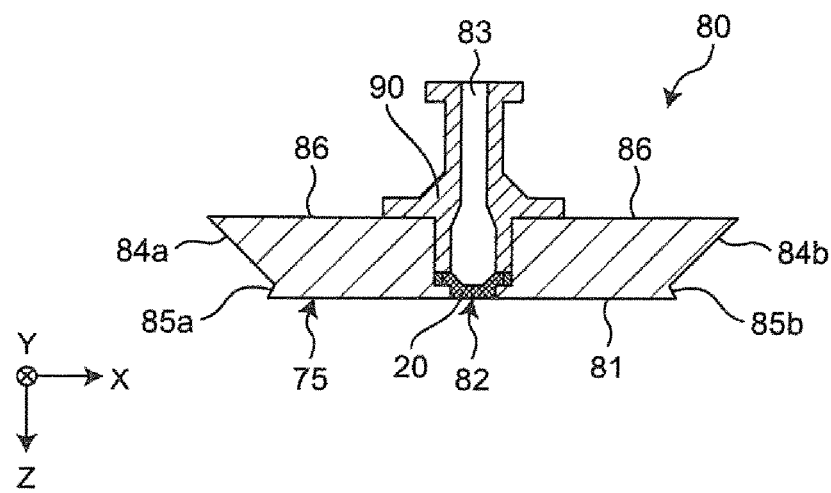
FIG. 17A is a schematic cross-sectional view of the second channel member of the channel member according to Embodiment 3 of the present invention.
Figure 17B:
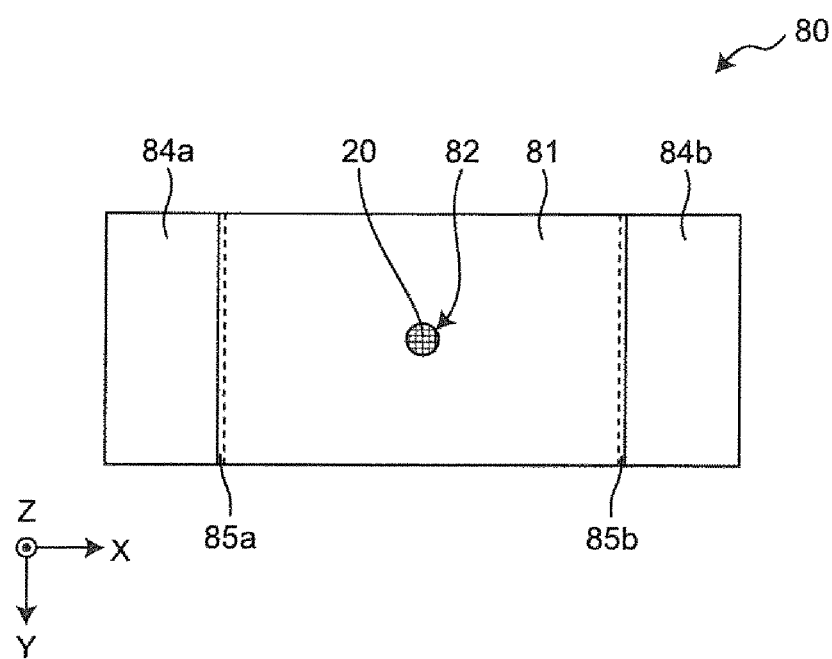
FIG. 17B is a schematic view, as seen from a projecting surface, of the second channel member of the channel member according to Embodiment 3 of the present invention.

FIG. 17A is a schematic cross-sectional view of the second channel member 80 of the channel member 10a according to Embodiment 3 of the present invention. FIG. 17B is a schematic view, as seen from the projecting surface 81, of the second channel member 80 of the channel member 10a according to Embodiment 3 of the present invention. FIGS. 17A and 17B each schematically illustrate the configuration of the second channel member 80 with the filter 20 attached to the second channel member 80. In FIGS. 17A and 17B, the second channel member 80 illustrated in FIG. 13 is depicted upside down for ease of description.

The second channel member 80 has the projection 87 that detachably mates with the recess 75 of the first channel member 70. The recess 75 and the projection 87 are detachably mated with each other without using another intervening component such as a screw. As illustrated in FIGS. 17A and 17B, the projecting surface 81 of the projection 87 of the second channel member 80 that contacts the recessed surface 76 of the recess 75 defines a flat surface. The second channel member 80 includes a discharge channel 83 extending in the Z direction. The discharge channel 83 has the opening 82 in the projecting surface 81 of the projection 87 placed over the groove 77. The filter 20 is positioned at the opening 82.

The second channel member 80 has a projecting mating surface 84 on the lateral side of the projection 87 to allow mating between the recess 75 and the projection 87. The projecting mating surface 84 defines a slope inclined with respect to the projecting surface 81 of the projection 87 that contacts the recessed surface 76 of the recess 75. In Embodiment 3, the projecting mating surface 84 has a third slope 84a, and a fourth slope 84b. The third slope 84a engages in mating relation with the first slope 78a, and the fourth slope 84b engages in mating relation with the second slope 78b.

The projecting mating surface 84 includes protrusions 85a and 85b, which protrude outwardly of the second channel member 80 and respectively mate with the notches 79a and 79b. More specifically, the third slope 84a includes a first protrusion 85a that mates with the first notch 79a of the first channel member 70, and the fourth slope 84b includes a second protrusion 85b that mates with the second notch 79b. The first protrusion 85a protrudes in the −X direction, and the second protrusion 85b protrudes in the +X direction. The slope of the first protrusion 85a is inclined with respect to the Z-axis by, for example, two degrees in the +X direction, and the slope of the second protrusion 85b is inclined with respect to the Z-axis by, for example, two degrees in the −X direction. It is to be noted that the first protrusion 85a and the second protrusion 85b are depicted in exaggerated form in the drawings.

The following describes, with reference to FIG. 15, the mating between the recess 75 of the first channel member 70 and the second channel member 80. The second channel member 80 is detachably attached to the first channel member 70 by mating the first protrusion 85a with the first notch 79a and mating the second protrusion 85b with the second notch 79b. This configuration helps keep the second channel member 80 from disengaging from the first channel member 70 in the Z direction. At this time, the mating between the first channel member 70 and the second channel member 80 is achieved by bringing the recessed surface 76 of the recess 75 (see FIG. 16A) and the projecting surface 81 of the projection 87 (see FIG. 17A) into surface contact with each other. Further, the mating between the first channel member 70 and the second channel member 80 is achieved by bringing the first slope 78a and the third slope 84a into surface contact with each other, and brining the second slope 78b and the fourth slope 84b into surface contact with each other. The first outer wall surface 74 of the first channel member 70 is flush with an outer wall surface 86 of the second channel member 80 located opposite to the projecting surface 81 of the projection 87.

As illustrated in FIG. 15, the third channel 73 is formed by positioning the projecting surface 81 of the projection 87 of the second channel member 80 over the opening 77a of the groove 77 of the first channel member 70. In other words, the groove 77 forms the third channel 73 as the second channel member 80 is mated with the recess 75 of the first channel member 70. The third channel 73 faces the filter 20 positioned at the opening 82 of the discharge channel 83 in the second channel member 80, and extends in the X direction.

The third channel 73 is connected to the first channel 71 via the first connection part 71a, and connected to the second channel 72 via the second connection part 72a. More specifically, the third channel 73 is connected to the first channel 71 via the first connection slope 71aa of the first connection part 71a, and connected to the second channel 72 via the second connection slope 72aa of the second connection part 72a. The first connection slope 71aa and the second connection slope 72aa are respectively inclined such that the first channel 71 and the second channel 72 decrease in cross-sectional area with increasing proximity to the third channel 73. This configuration helps prevent an abrupt change in the velocity of liquid flow from the first channel 71 to the third channel 73, and an abrupt change in the velocity of liquid flow from the third channel 73 to the second channel 72.

Figure 18:
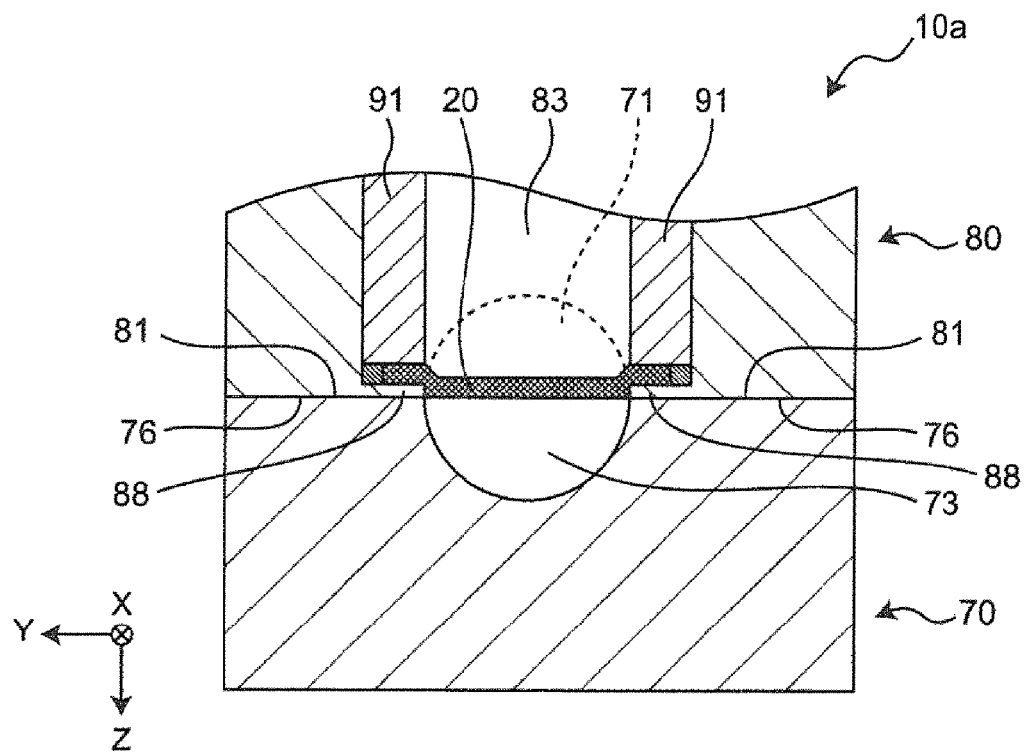
FIG. 18 is a longitudinal sectional view, taken at the position where a filter is positioned, of a portion of the channel member according to Embodiment 3 of the present invention.

FIG. 18 is a longitudinal section, taken at the position where the filter 20 is positioned, of a portion of the channel member 10a according to Embodiment 3 of the present invention. As illustrated in FIG. 18, the third channel 73 has a smaller cross-sectional area than the first and second channels 71 and 72. More specifically, the third channel 73, at which the filter 20 is positioned, has a smaller cross-sectional area than the first channel 71. In other words, the portion of the third channel 73 where the filter 20 is positioned has a smaller cross-sectional area than the first channel 71. In the preferred embodiment, the third channel 73 has half the cross-sectional area of each of the first and second channels 71 and 72, which are in the shape of a circular tube. More specifically, the third channel 73 extends in the same direction (X direction) as the first channel 71, and is formed in the shape of a semi-circular tube with a semi-circular cross-section. The third channel 73 thus has the same cross-sectional shape as the lower half of each of the first and second channels 71 and 72. This configuration helps prevent an abrupt change in the velocity of liquid flow from the first channel 71 to the third channel 73, and an abrupt change in the velocity of liquid flow from the third channel 73 to the second channel 72. The above-mentioned configuration, in which the first and second channels 71 and 72 are formed in the shape of a circular tube and the third channel 73 is formed in the shape of a semi-circular tube, can also help reduce accumulation of the target substance at the bottom.

The second channel member 80 is, for example, made of polyoxymethylene (POM), polypropylene (PP), or polyether ether ketone (PEEK). There are, for example, four possible combinations of the first channel member 70 and the second channel member 80 described below. In a first combination, the first channel member 70 is made of polystyrene, and the second channel member 80 is made of polypropylene. In a second combination, the first channel member 70 is made of polymethyl methacrylate, and the second channel member 80 is made of polyoxymethylene. In a third combination, the first channel member 70 is made of polystyrene, and the second channel member 80 is made of polyether ether ketone. In the fourth combination, the first channel member 70 is made of polyphenylene sulfide, and the second channel member 80 is made of polyether ether ketone.

The first combination is a preferred combination of materials of the first and second channel members 70 and 80. Using the first combination can improve the workability and biocompatibility of the first and second channel members 70 and 80. Further, the first combination ensures high transparency of the first and second channel members 70 and 80. This allows internal fluid flow to be easily observed without detaching the second channel member 80 from the first channel member 70. By using different materials for the first and second channel members 70 and 80 as described above, the first channel member 70 can be improved in impact resistance and wear resistance, and the second channel member 80 can be made of a soft material to allow for easy mating with the first channel member 70.

Figure 19:
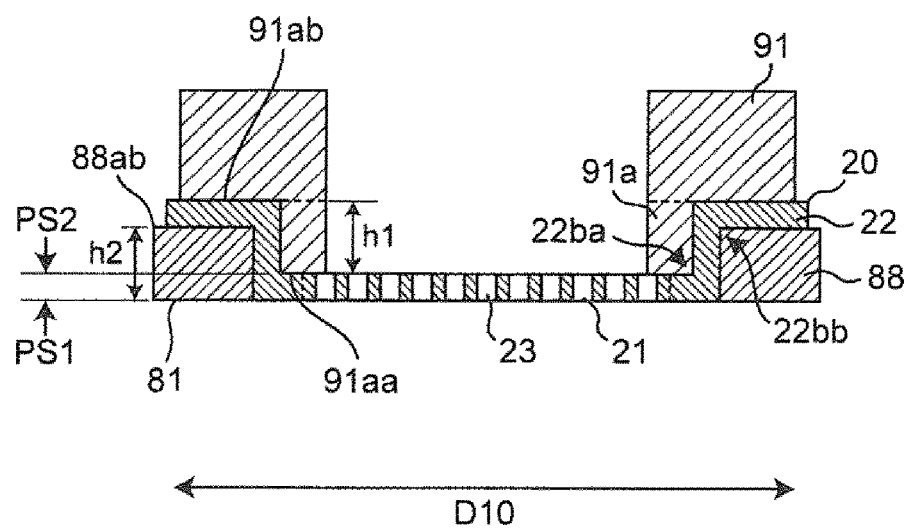
FIG. 19 is an enlarged cross-sectional view of the filter illustrated in FIG. 18.

FIG. 19 is an enlarged cross-sectional view of the filter 20 illustrated in FIG. 18. As illustrated in FIG. 19, the holding part 22 is formed by bending the outer periphery portion of the filter 20 in the direction of the second major surface PS2. The holding part 22 is a portion of the filter 20 positioned closer to the outer edge of the filter 20 than the position where the filtering part 21 begins to bend. In Embodiment 3, the holding part 22 has a first bent part 22*ba*, and a second bent part 22*bb*. The first bent part 22*ba* is a portion of the holding part 22 that is bent in the direction of the second major surface PS2 of the filtering part 21. The second bent part 22*bb* is a portion of the holding part 22 located closer to the outer edge of the filter 20 than the first bent part 22*ba* and bent in a direction of extension D10 in which the filtering part 21 extends. In Embodiment 3, the first bent part 22*ba* is bent in the direction of the second major surface PS2 from the first major surface PS1 of the filtering part 21. The second bent part 22*bb* is bent in a direction parallel to the first and second major surfaces PS1 and PS2 of the filtering part 21. Thus, in the area between the first bent part 22*ba* and the second bent part 22*bb*, the holding part 22 extends in the direction of the second major surface PS2 from the first major surface PS1 of the filtering part 21. In the area closer to the outer edge of the filter 20 than the second bent part 22*bb*, the holding part 22 extends in the direction D10 in which the filtering part 21 extends, that is, in the direction parallel to the first and second major surfaces PS1 and PS2 of the filtering part 21. The direction D10 in which the filtering part 21 of the filter 20 extends includes a direction toward the outer edge of the filter 20, and a direction away from the outer edge of the filter 20. In Embodiment 3, as described above, the second bent part 22*bb* of the holding part 22 is bent toward the outer edge of the filter 20 relative to the first bent part 22*ba*. The first bent part 22*ba* and the second bent part 22*bb* may be, for example, bent in an arcuate shape, or bent at an obtuse angle.

The filter 20 is sandwiched between a first frame part 88 of the second channel member 80, and a second frame part 91 of the holder 90.

The first frame part 88 is formed inside the second channel member 80, and used to sandwich the holding part 22 of the filter 20 between the first frame part 88 and the second frame part 91 of the holder 90. More specifically, the first frame part 88 protrudes from the side wall of the discharge channel 83. The first frame part 88 is formed in an annular (e.g., circular ring) shape, and adapted to receive the second frame part 91 of the holder 90 with the holding part 22 of the filter 20 sandwiched therebetween. The first frame part 88 is located closer to the outer edge of the filter 20 than the boundary between the filtering part 21 and the holding part 22. The first frame part 88 is in contact with a side of the holding part 22 located proximate to the first major surface PS1 of the filter 20. The boundary between the filtering part 21 and the holding part 22 is the position where the filter 20 begins to bend in the direction of the second major surface PS2 in the outer periphery portion of the filter 20. In Embodiment 3, the first frame part 88 is located outward in the direction of extension D10 relative to the bending position of the first bent part 22*ba*. At a location proximate to the first major surface PS1 of the filter 20, the first frame part 88 is in contact with the holding part 22 but not in contact with the filtering part 21. In Embodiment 3, with the holder 90 viewed in the Z direction, the space enclosed by the first frame part 88 serves as the opening 82 of the discharge channel 83.

The second frame part 91 is provided on the outer wall surface of the holder 90, and used to sandwich the holding part 22 of the filter 20 between the second frame part 91 and the first frame part 88. More specifically, the second frame part 91 is formed in a cylindrical shape. The second frame part 91 has, in its inner periphery portion, a first stepped part 91*a* that projects toward a portion of the filtering part 21 of the filter 20. The second frame part 91 is located inside the first frame part 88 with the holding part 22 of the filter 20 sandwiched therebetween. The first stepped part 91*a* of the second frame part 91 is fit inside the first frame part 88. More specifically, at a location proximate to the second major surface PS2 of the filter 20, the second frame part 91 is in contact with an area extending over a portion of the holding part 22 and a portion of the filtering part 21.

The first stepped part 91*a* of the second frame part 91 serves to push the filtering part 21 in the direction of the first major surface PS1 from the second major surface PS2, thus regulating the position of the first major surface PS1 of the filtering part 21.

The first stepped part 91*a*, which projects toward a portion of the filtering part 21, has a first contact surface 91*aa* that pushes the filtering part 21 in the direction of the first major surface PS1 from the second major surface PS2. Although a side of the filtering part 21 defining the second major surface PS2 contacts the second frame part 91, a side of the filtering part 21 defining the first major surface PS1 does not contact the first frame part 88. This means that the position of the filtering part 21 is not restricted by the first frame part 88. Thus, varying the height h1 of the first stepped part 91*a* of the second frame part 91 makes it possible to freely determine the position where the filtering part 21 is to be held. In other words, varying the height h1 of the first stepped part 91*a* of the second frame part 91 makes it possible to freely determine the position of the first major surface PS1 of the filtering part 21. The height h1 of the first stepped part 91*a* is herein defined as the distance between the first contact surface 91*aa* of the first stepped part 91*a* of the second frame part 91, and a second contact surface Slab of the second frame part 91.

In Embodiment 3, the height of the first stepped part 91*a* is determined such that the first major surface PS1 of the filtering part 21 is substantially flush with the projecting surface 81. More specifically, the height h1 of the first stepped part 91*a* is substantially equal to the distance h2 between a third contact surface 88*ab* of the first frame part 88 and the projecting surface 81. The expression "substantially equal" as used herein means that the difference between the distance h1 and the distance h2 is within the range of ±10%.

Figure 20:
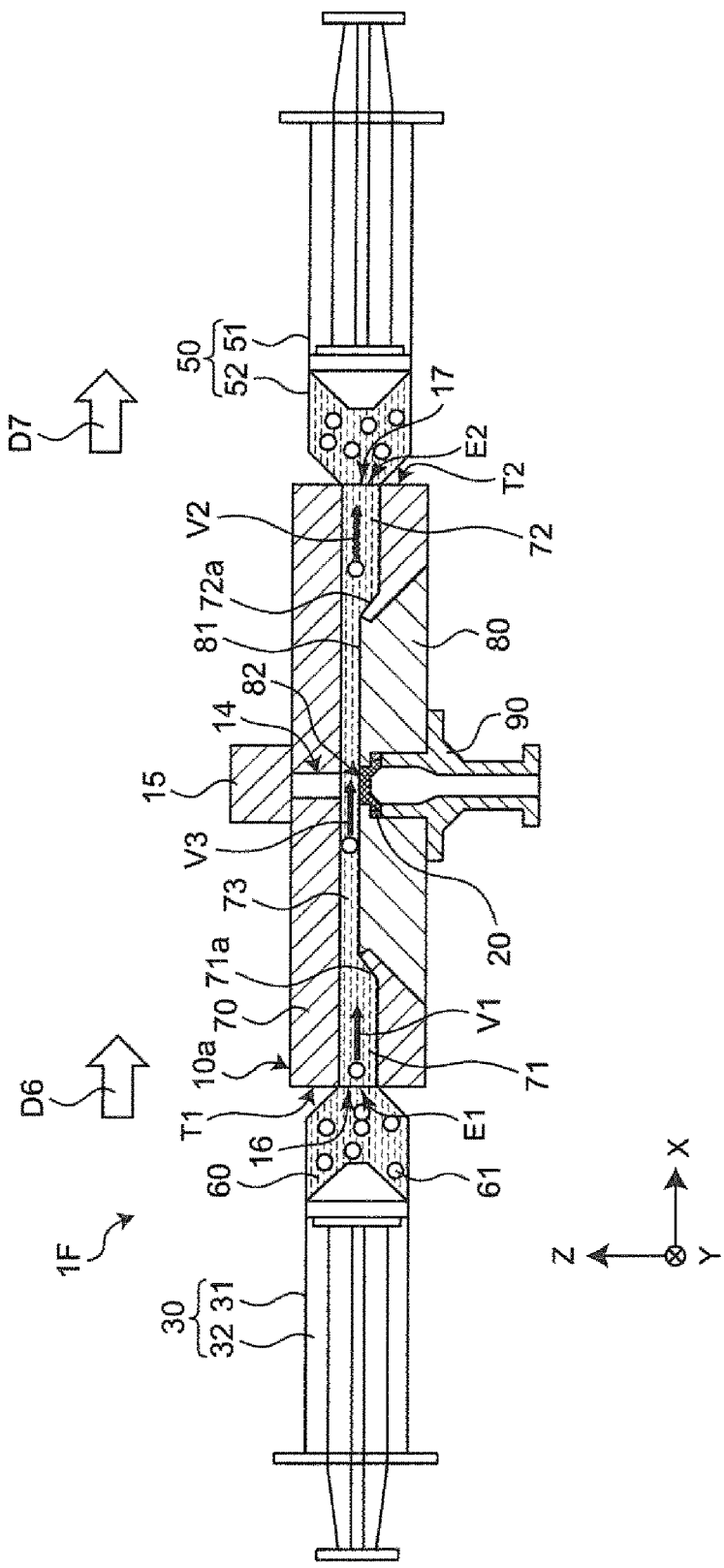
FIG. 20 schematically illustrates an example of filtration being performed by using the filtration device according to Embodiment 3 of the present invention.

The following describes, with reference to FIG. 20, how the filtration device 1F operates in filtering the liquid 60 including the target substance 61. FIG. 20 is a cross-sectional view of the filtration device 1F depicted in FIG. 13, illustrating how the liquid 60 including the target substance 61 flows through each channel in the channel member 10*a*. As illustrated in FIG. 20, the volume of the first space S1 in the first container 30 is changed to allow liquid 60 in the first container 30 to be transferred to the first channel 71 of the channel member 10*a*. More specifically, the plunger 32 of the first container 30 is pushed in a direction D6, which is a direction toward the distal end of the outer cylinder 31, thus decreasing the volume of the first space S1 in the first container 30. At this time, the plunger 52 of the second container 50 is pulled in a direction D7, which is a direction away from the distal end of the outer cylinder 51, thus increasing the volume of the second space S2 in the second container 50. As a result, the liquid 60 contained in the first space S1 in the first container 30 moves through the first channel 71, the third channel 73, and the second channel 72 in this order to the second space S2 in the second container 50.

In the filtration device 1F, the filter 20 is positioned at the third channel 73. Cross-flow filtration is thus performed as the liquid 60 passes through the third channel 73. More specifically, the target substance 61 is trapped (blocked from passing through) by the filter 20, and a portion of the liquid 60 flowing in the third channel 73 passes through the filter 20 and is discharged through the discharge channel 83. The remainder of the liquid 60 flowing in the third channel 73 then travels into the second channel 72.

At this time, due to the smaller cross-sectional area of the third channel 73 than the first and second channels 71 and 72, the liquid 60 flows through the third channel 73 at a velocity V3 which is higher than the velocities V1 and V2 at which the liquid 60 respectively flows through the first and second channels 71 and 72.

In the first connection part 71*a* connecting the first channel 71 with the groove 77, and in the second connection part 72*a* connecting the second channel 72 with the groove 77, the first and second channels 71 and 72 decrease in cross-sectional area with increasing proximity to the groove 77. This configuration helps prevent an abrupt change in the velocity of the flow of the liquid 60 from the first channel 71 to the third channel 73, and an abrupt change in the velocity of the flow of the liquid 60 from the third channel 73 to the second channel 72.

The mating between the first channel member 70 and the second channel member 80 is achieved by bringing the recessed surface 76 of the recess 75 and the projecting surface 81 of the projection 87 into surface contact with each other. This configuration helps keep the liquid 60 in the third channel 73 from leaking out through the recessed surface 76. The mating between the first channel member 70 and the second channel member 80 is also achieved by bringing the recessed mating surface 78 and the projecting mating surface 84 into surface contact with each other. More specifically, the mating between the first channel member 70 and the second channel member 80 is achieved by bringing the first slope 78*a* and the third slope 84*a* into surface contact with each other, and bringing the second slope 78*b* and the fourth slope 84*b* into surface contact with each other. This configuration helps keep the liquid 60 in the third channel 73 from leaking out through the recessed mating surface 78.

The filtration device 1F according to Embodiment 3 can have the following effects.

The channel member 10*a* of the filtration device 1F includes the first channel member 70, and the second channel member 80. The first channel member 70 has the recess 75, the groove 77, and the first and second channels 71 and 72. The recess 75 is recessed inward from the first outer wall surface 74. The groove 77 has the opening 77*a* in the recessed surface 76 of the recess 75. The first and second channels 71 and 72 are each defined by a through-hole connected to the groove 77. The first channel member 70 also has the first connection part 71*a* that connects the groove 77 with the first channel 71, and the second connection part 72*a* that connects the groove 77 with the second channel 72. The second channel member 80 has the projection 87 that detachably mates with the recess 75 of the first channel member 70. The second channel member 80 includes the discharge channel 83 that has the opening 82 in the projecting surface 81 of the projection 87 placed over the groove 77 of the first channel member 70. The third channel 73 of the channel member 10*a* is formed by positioning the projecting surface 81 of the projection 87 of the second channel member 80 over the opening 77*a* of the groove 77 of the first channel member 70. The third channel 73 is connected to the first channel 71 via the first connection part 71*a*, and connected to the second channel 72 via the second connection part 72*a*. The third channel 73 has a smaller cross-sectional area than the first and second channels 71 and 72. The filter 20 is positioned at the third channel 73. The first space S1 in the first container 30 communicates with the first channel 71, and the second space S2 in the second container 50 communicates with the second channel 72.

The above-mentioned configuration allows the liquid 60 to flow through the third channel 73, at which the filter 20 is positioned, faster than through the first and second channels 71 and 72. This helps reduce clogging of the filter 20 by the target substance 61. If the target substance 61 is a cell, the above-mentioned configuration also helps minimize a decrease in the activity of the cell or damage to the cell.

The channel member 10*a* is formed by the first and second channel members 70 and 80 that are separate from each other. Consequently, the cross-sectional area of the third channel 73 can be easily changed by changing the shape of the second channel member 80. For example, the projecting surface 81 of the projection 87 of the second channel member 80 may be provided with a protruding portion, and the protruding portion may be extended to the vicinity of the lower end portion (end portion in the −Z direction) of the groove 77 to further reduce the cross-sectional area of the third channel 73. The above-mentioned configuration also allows the third channel 73 to be easily formed by the first channel member 70 and the second channel member 80. Further, a second outer wall surface of the first channel member 70, which is the wall surface opposite to the first outer wall surface 74, is placed on a placement surface. This configuration helps ensure that, when the second channel member 80 is detached from the first channel member 70, the target substance 61 can be observed and sampled while allowing the first channel member 70 to keep storing the liquid 60 including the target substance 61. Further, the liquid 60 including the target substance 61 can be easily collected from the groove 77.

The recess 75 of the first channel member 70, and the projection 87 of the second channel member 80 may be detachably mated with each other without using another intervening component.

The above-mentioned configuration eliminates the need for a screw or other such component. The second channel member 80 can be thus easily attached to or detached from the first channel member 70.

The first channel member 70 has the recessed mating surface 78 on the lateral side of the recess 75 to allow mating between the recess 75 and the projection 87. The second channel member 80 has the projecting mating surface 84 on the lateral side of the projection 87 to allow mating between the recess 75 and the projection 87. The recessed mating surface 78 includes the notches 79*a* and 79*b* recessed inwardly of the first channel member 70. The projecting mating surface 84 includes the protrusions 85*a* and 85*b*, which protrude outwardly of the second channel member 80 and respectively mate with the notches 79*a* and 79*b*. The second channel member 80 is detachably attached to the first channel member 70 by mating the protrusions 85*a* and 85*b* respectively with the notches 79*a* and 79*b*.

The above-mentioned configuration facilitates detachably attaching the second channel member 80 to the first channel member 70.

The recessed mating surface 78 defines a surface inclined with respect to the recessed surface 76 of the recess 75. The projecting mating surface 84 defines the slopes 84*a* and 84*b* inclined with respect to the projecting surface 81 of the projection 87 that contacts the recessed surface 76 of the recess 75. The mating between the first channel member 70 and the second channel member 80 is achieved by bringing the recessed mating surface 78 and the projecting mating surface 84 into surface contact with each other.

The above-mentioned configuration helps ensure that, at the location of the lateral side of the recess 75, the first channel member 70 and the second channel member 80 make contact over an increased area. This helps further reduce leakage of the liquid 60 flowing in the third channel 73.

The recessed surface 76 of the recess 75 of the first channel member 70 defines a flat surface. The projecting surface 81 of the projection 87 of the second channel member 80 defines a flat surface. The mating between the first channel member 70 and the second channel member 80 is achieved by bringing the recessed surface 76 of the recess 75 and the projecting surface 81 of the projection 87 into surface contact with each other.

The above-mentioned configuration helps ensure that, at the location of the recessed surface 76 of the recess 75, the first channel member 70 and the second channel member 80 make contact over an increased area. This helps further reduce leakage of the fluid flowing in the first channel member 70.

The filter 20 has the first major surface PS1 and the second major surface PS2 that face each other. The first major surface PS1 is located adjacent to the third channel 73, and the second major surface PS2 is located adjacent to the discharge channel 83. The first major surface PS1 and the projecting surface 81 are flush with each other.

The above-mentioned configuration helps increase the velocity at which the liquid 60 flows near the filter 20.

The filter 20 is attached to the second channel member 80. This allows the filter 20 to be easily replaced by detaching the second channel member 80 from the first channel member 70.

The groove 77 is provided linearly. This helps increase the velocity at which the liquid 60 flows through the third channel 73 defined by the groove 77.

Although the foregoing description of Embodiment 3 is directed to the case where the first and second channels 71 and 72 have the same cross-sectional area, this is not to be construed restrictively. The first and second channels 71 and 72 may have different cross-sectional areas.

Figure 21:
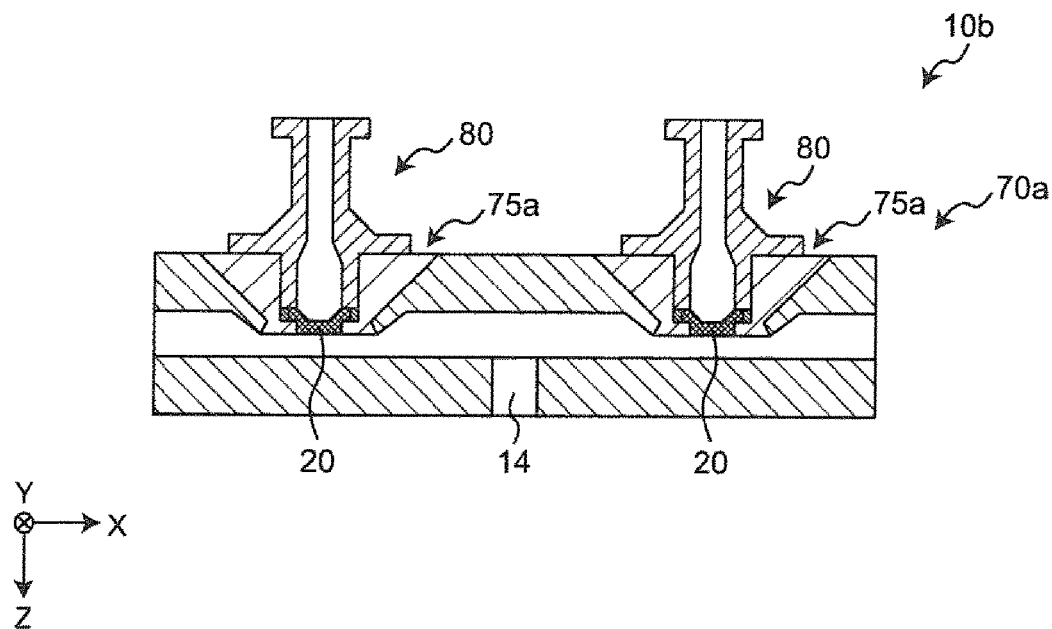
FIG. 21 is a schematic cross-sectional view of a channel member according to a modification.

Although the foregoing description of Embodiment 3 is directed to the case where the first channel member 70 has a single recess 75, the invention is not so limited. FIG. 21 is a schematic cross-sectional view of a channel member 10*b* according to a modification. As illustrated in FIG. 21, a first channel member 70*b* may have a plurality of recesses 75*a*. Each recess 75*a* of the first channel member 70*b* mates with the second channel member 80 to which the filter 20 is attached. This configuration makes it possible to use a plurality of filters 20 to filter the liquid 60 including the target substance 61. This leads to further improved filtration efficiency.

Although the foregoing description of Embodiment 3 is directed to the case where the angle θ1 formed by the first slope 78*a* and the recessed surface 76, and the angle θ2 formed by the second slope 78*b* and the recessed surface 76 are 45 degrees, the invention is not so limited. The angles θ1 and θ2 may not necessarily be 45 degrees. The angles θ1 and θ2 may differ from each other.

Although the foregoing description of Embodiment 3 is directed to the case where the first notch 79*a* is provided in an end portion of the first slope 78*a* located adjacent to the recessed surface 76, and the second notch 79*b* is provided in an end portion of the second slope 78*b* located adjacent to the recessed surface 76, the invention is not so limited. The first notch 79*a* may be provided in a portion of the first slope 78*a* other than the end portion located adjacent to the recessed surface 76. The second notch 79*b* may be provided in a portion of the second slope 78*b* other than the end portion located adjacent to the recessed surface 76.

Although the foregoing description of Embodiment 3 is directed to the case where the first notch 79*a* is inclined with respect to the Z-axis by two degrees in the +X direction, and the second notch 79*b* is inclined with respect to the Z-axis by two degrees in the −X direction, the invention is not so limited. Although the foregoing description is directed to the case where the first protrusion 85*a* is inclined with respect to the Z-axis by two degrees in the +X direction, and the second protrusion 85*b* is inclined with respect to the Z-axis by two degrees in the −X direction, this is not to be construed restrictively. The first notch 79*a*, the second notch 79*b*, the first protrusion 85*a*, and the second protrusion 85*b* may not necessarily be inclined by two degrees.

Figure 22:
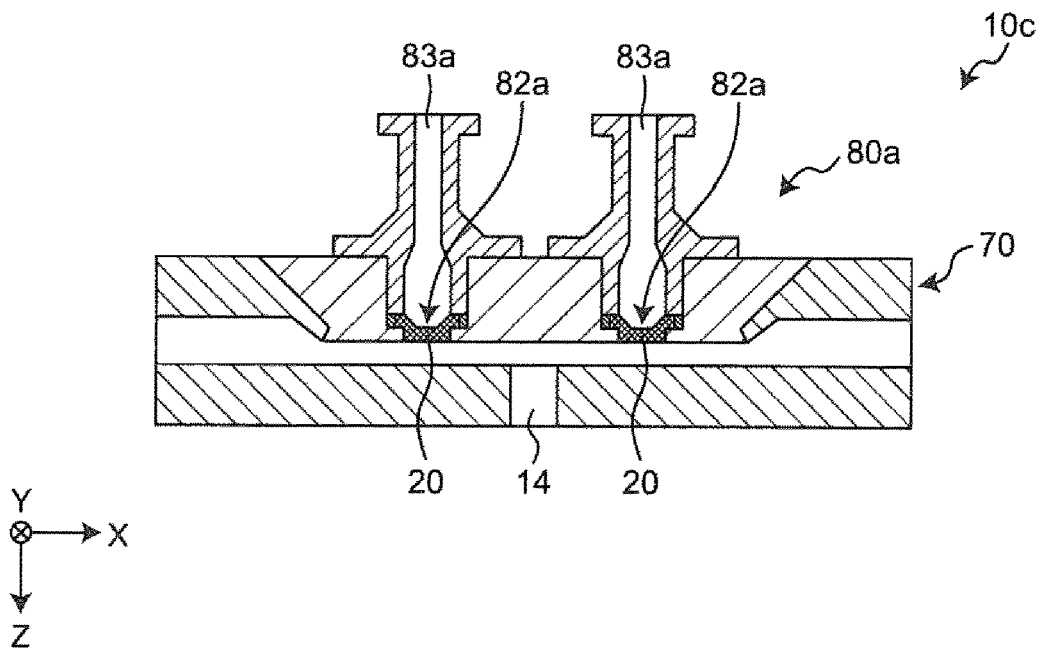
FIG. 22 is a schematic cross-sectional view of a channel member according to another modification.

Although the foregoing description of Embodiment 3 is directed to the case where the second channel member 80 is provided with a single opening 82, the invention is not so limited. FIG. 22 is a schematic cross-sectional view of a channel member 10*c* according to a modification. As illustrated in FIG. 22, a second channel member 80*a* may be provided with a plurality of discharge channels 83*a* each having an opening 82*a*, with the filter 20 attached to the opening 82*a* of each discharge channel 83*a*. This configuration makes it possible to use a plurality of filters 20 to filter the liquid 60 including the target substance 61. This leads to improved filtration efficiency.

Although the foregoing description of Embodiment 3 is directed to the case where the first outer wall surface 74 of the first channel member 70 is flush with the outer wall surface 86 of the second channel member 80 located opposite to the projecting surface 81, and the second outer wall surface of the first channel member 70 located opposite to the first outer wall surface 74 is parallel to the first outer wall surface 74, the invention is not so limited. For example, the outer wall surface 86 of the second channel member 80 may be positioned higher than the first outer wall surface 74 of the first channel member 70 in the +Z direction. The second outer wall surface of the first channel member 70 may be formed in a shape different from the first outer wall surface 74, for example, a curved shape.

Although the foregoing description of Embodiment 3 is directed to the case where, in the first connection part 71*a* connecting the first channel 71 with the groove 77, and in the second connection part 72*a* connecting the second channel 72 with the groove 77, the first and second channels 71 and 72 decrease in cross-sectional area with increasing proximity to the groove 77, the invention is not so limited. Other configurations may be employed as long as the first channel member 70 and the second channel member 80 mate with each other such that the third channel 73 has a smaller cross-sectional area than the first and second channels 71 and 72.

Figure 23:
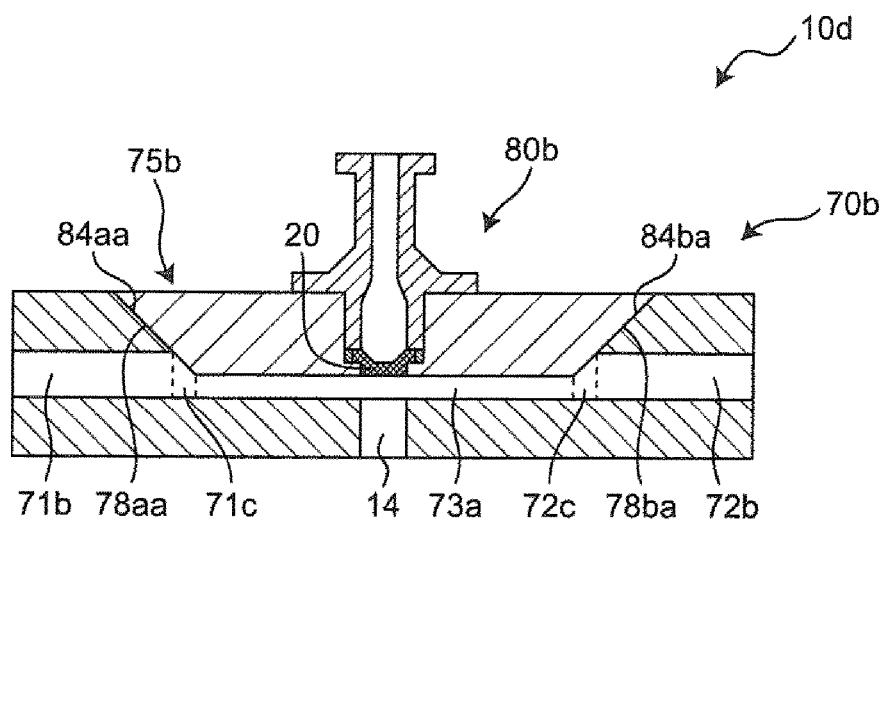
FIG. 23 is a schematic cross-sectional view of a channel member according to another modification.

FIG. 23 is a schematic cross-sectional view of a channel member 10*d* according to a modification. As illustrated in FIG. 23, a third channel 73*a* may be formed such that, with a recess 75*b* of the first channel member 70*b* mated with a second channel member 80*b*, a portion of a projecting mating surface 84*aa* of the second channel member 80*b*, and a portion of a projecting mating surface 84*ba* of the second channel member 80*b* respectively reduce the cross-sectional areas of a first channel 71*b* and a second channel 72*b*. In other words, a first connection part 71*c* connecting the first channel 71*b* with the third channel 73*a* may be defined by the projecting mating surface 84*aa* of the second channel member 80. A second connection part 72*c* connecting the second channel 72*b* with the third channel 73*a* may be defined by the projecting mating surface 84*ba* of the second channel member 80.

The above-mentioned configuration as well helps reduce clogging of the filter 20 by the target substance 61. If the target substance 61 is a cell, the above-mentioned configuration also helps minimize a decrease in the activity of the cell or damage to the cell. The above-mentioned configuration also allows the shape of the third channel 73*a* to be changed easily by changing the shape of the second channel member 80*b*. For example, by extending the second channel member 80*b* toward the lower end portion (end portion in the −Z direction) of the groove 77, the cross-sectional area of the third channel 73*a* can be further reduced.

Although the foregoing description of Embodiment 3 is directed to the case where, in the second connection part 72*a* connecting the second channel 72 with the groove 77, the second channel 72 decreases in cross-sectional area with increasing proximity to the groove 77, the invention is not so limited. For example, the second channel 72, the second connection part 72*a*, and the third channel 73 may have the same cross-sectional area. This configuration as well makes it possible to minimize an increase in the velocity of the liquid 60 through the first channel 71 while increasing the velocity of the liquid 60 through the third channel 73 that faces the filter 20.

Although the foregoing description of Embodiment 3 is directed to the case where the recessed mating surface 78 includes the notches 79*a* and 79*b*, and the projecting mating surface 84 includes the protrusions 85*a* and 85*b*, the invention is not so limited. For example, the recessed mating surface 78 may include a protrusion, and the projecting mating surface 84 may include a notch. This configuration as well facilitates the mating between the recess 75 and the projection 87.

Although the foregoing description of Embodiment 3 is directed to the case where the filter 20 is attached to the second channel member 80, the invention is not so limited As long as the filter 20 is positioned at the third channel 73, the filter 20 may be attached to, for example, the first channel member 70.

Although the foregoing description of Embodiment 3 is directed to the case where the second channel member 80 is detachably attached to the first channel member 70 by mating the protrusions 85*a* and 85*b* respectively with the notches 79*a* and 79*b*, the invention is not so limited. The second channel member 80 may be detachably attached to the first channel member 70 by threaded engagement.

Figure 24:
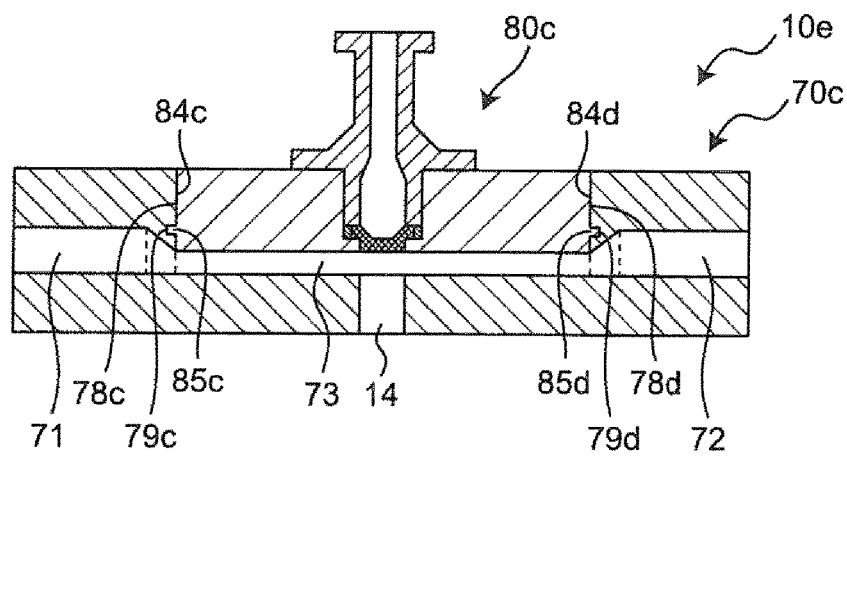
FIG. 24 is a schematic cross-sectional view of a channel member according to another modification.

Although the foregoing description of Embodiment 3 is directed to the case where, for the channel member 10*a*, the recessed mating surface 78 defines a slope inclined with respect to the recessed surface 76 of the recess 75, and the projecting mating surface 84 defines a slope inclined with respect to the projecting surface 81 of the projection 87 that contacts the recessed surface 76 of the recess 75, the invention is not so limited. Alternatively, for example, a channel member 10*e* configured as illustrated in FIG. 24 may be employed. As illustrated in FIG. 24, a recessed mating surface of a first channel member 70*c* includes a first mating surface 78*c*, and a second mating surface 78*d*. The first mating surface 78*c* and the second mating surface 78*d* are not formed as inclined surfaces. More specifically, the first mating surface 78*c* and the second mating surface 78*d* extend in a direction (Z direction) orthogonal to the direction in which the third channel 73 extends. A projecting mating surface of a second channel member 80*c* includes a third mating surface 84*c*, and a fourth mating surface 84*d*. The third mating surface 84*c* and the fourth mating surface 84*d* are not formed as inclined surfaces. More specifically, the third mating surface 84*c* and the fourth mating surface 84*d* extend in the direction (Z direction) orthogonal to the direction in which the third channel 73 extends.

The first mating surface 78c includes a first notch 79c notched in a direction (−X direction) in which the first channel 71 extends. The second mating surface 78d includes, in its end portion adjacent to the recessed surface 76, a second notch 79d notched in a direction (+X direction) in which the second channel 72 extends. The third mating surface 84c includes a first protrusion 85c that mates with the first notch 79c of the first channel member 70c, and the fourth mating surface 84d includes a second protrusion 85d that mates with the second notch 79d. This configuration as well facilitates detachably attaching the second channel member 80c to the first channel member 70c.

Although the present invention has been described in sufficient detail by way of preferred embodiments with reference to the accompanying drawings, various modifications and alterations will be apparent to those skilled in the art. Such modifications and alterations are to be understood as falling within the scope of the invention as defined by the appended claims without departing therefrom.

INDUSTRIAL APPLICABILITY the filtration device according to the present invention allows for improved recovery of nucleated cells and is therefore useful for applications involving separation of nucleated cells from cell suspensions.

REFERENCE SIGNS LIST 1A, 1B, 1C, 1D, 1E, 1F filtration device
10, 10a, 10b, 10c, 10d, 10e channel member
11 channel
12 closing member
13 opening
14 collection hole
15 cap
16 attachment part (first attachment part)
17 attachment part (second attachment part)
20 filter
21 filtering part
22 holding part
23 through-hole
24 filtering body part
30, 30a container (first container)
31 outer cylinder
32 plunger
40 collection device
50, 50a second container
51 outer cylinder
52 plunger
60 liquid
61 target substance
70, 70b first channel member
71, 71b first channel
71a, 71c first connection part
72, 72b second channel
72a, 72c second connection part
73, 73a third channel
74 first outer wall surface
75, 75a, 75b recess
76 recessed surface
77 groove
77a opening
78, 78aa, 78ba recessed mating surface
78a first slope
78b second slope
78c first mating surface
78d second mating surface
79a first notch
79b second notch
79c first notch
79d second notch
80, 80a, 80b, 80c second channel member
81 projecting surface
82, 82a opening
83, 83a discharge channel
84 projecting mating surface
84a third slope
84aa projecting mating surface
84b fourth slope
84ba projecting mating surface
84c third mating surface
84d fourth mating surface
85a first protrusion
85b second protrusion
85c first protrusion
85d second protrusion
86 outer wall surface
87 projection
88 first frame part
90 holder
91 second frame part
91a first stepped part
91aa first contact surface
91ab second contact surface
PS1 first major surface
PS2 second major surface
D1, D2, D3, D4, D5, D6, D7, D10 direction
E1 one end of channel
E2 other end of channel
T1 one end of channel member
T2 other end of channel member

The invention claimed is:

1. A filtration device comprising:
first container have a first space of variable volume that can contain a liquid which includes a target substance to be separated by filtration;
a second container have a second space of variable volume that can contain the liquid;
a channel member having first and second subsections that are removably attached to one another between an operative position, where they are coupled to one another and define a channel having first and second ends, and a separated position, where they are separated from one another, the channel having first, second and third channel portions, the third channel portion being located between the first and second channel portions, the first and second channel portions having larger cross sectional areas than the third channel portion, the third channel portion extending in the same direction as the first channel portion and having the shape of a semi-circular tube with a semi-circular cross section;
the first and second containers being in fluid communication with the first and second ends of the channel, respectively, such that the liquid can be moved between the first container, the channel, and the second container by varying the volume of the first and/or second spaces;
an opening extending from the channel to a first position outside of the channel member;
a collection hole, separate from the opening, extending from the channel to a second position outside of the channel member;

a filter located inside the channel member and positioned at the opening for filtering at least some of the liquid that passes into the channel and through the filter such that at least part of the target substance remains in the channel; and a cap closing the collection hole but being penetrable so that at least part of the target substance can be removed from the channel through the cap.

2. The filtration device according to claim 1, wherein the channel extends in a longitudinal direction and the opening extends in a direction transverse to the longitudinal direction.

3. The filtration device according to claim 1, wherein at least a portion of an inner wall of the first container is movable to change the volume of the first space and to cause at least part of the liquid to move from the first space to the channel.

4. The filtration device according to claim 1, wherein the first container is a syringe.

5. The filtration device according to claim 1, wherein each of the first and second containers is a syringe.

6. A filtration method for filtering a target substance contained in a liquid using the filtration device of claim 1, the filtration method comprising:

supplying at least some of the liquid contained in the first space to the channel by changing a volume of the first space;

passing at least part of the liquid through the filter such that at least some of the target substance remains in the channel; and removing at least some of the target substance located in the channel via the collection hole.

7. A filtration method for filtering a target substance contained in a liquid using the filtration device of claim 1, the filtration method comprising:

moving at least some of the liquid contained in the first space to the second space via the channel by changing the volume of the first space; and passing at least part of the liquid through the filter as it moves through the channel between the first and second spaces.

8. The filtration method according to claim 7, further comprising:

after the at least some of the liquid has been supplied to the second space, supplying at least first part of the liquid contained in the second space to the first space via the channel by changing the volume of the second space; and passing at least a second part of the liquid through the filter as it moves through the channel from the second space to the first space.

9. The filtration method according to claim 8, further comprising, after at least a third part of the liquid has been moved from the second space to the first space via the channel, moving at least fourth part of the liquid contained in the first space to the second space via the channel, and thereafter moving at least a fifth part of the liquid in the second space back to the first space via the channel such that each time the liquid moves through the channel, at least some of the liquid is passed through the filter.

10. The filtration method according to claim 7, further comprising collecting at least a portion of the target substance present in the channel via the collection hole.

11. The filtration method according to claim 8, further comprising collecting at least a portion of the target substance present in the channel via the collection hole.

12. The filtration method according to claim 9, further comprising collecting at least a portion of the target substance present in the channel via the collection hole.

13. The filtration device according to claim 1, wherein the cross sections of the first and second channel portions are constant and are connected to the third channel portion via respective transition portions each having varying cross sections.

14. The filtration device according to claim 13, wherein the first and second channel portions are circular in cross section and the first and second transition portions taper from the first and second channel portions, respectively, to the third channel portion.

* * * * *